US008088726B2

(12) United States Patent
Yamamoto et al.

(10) Patent No.: US 8,088,726 B2
(45) Date of Patent: Jan. 3, 2012

(54) PROCESS FOR PRODUCING SUSTAINED-RELEASE COMPOSITION

(75) Inventors: Kazumichi Yamamoto, Kyoto (JP); Kazuhiro Saito, Hyogo (JP); Tetsuo Hoshino, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1626 days.

(21) Appl. No.: 10/518,914

(22) PCT Filed: Jun. 24, 2003

(86) PCT No.: PCT/JP03/07950
§ 371 (c)(1),
(2), (4) Date: Dec. 23, 2004

(87) PCT Pub. No.: WO04/000363
PCT Pub. Date: Dec. 31, 2003

(65) Prior Publication Data
US 2005/0214330 A1 Sep. 29, 2005

(30) Foreign Application Priority Data

Jun. 25, 2002 (JP) .................................. 2002-185352

(51) Int. Cl.
*A61K 38/00* (2006.01)
*A61K 51/00* (2006.01)
(52) U.S. Cl. ......... 514/1.1; 530/300; 530/325; 530/326; 530/330; 424/1.69
(58) Field of Classification Search .................. None
See application file for complete search history.

(56) References Cited

U.S. PATENT DOCUMENTS

| 4,211,769 | A | | 7/1980 | Okada et al. | |
|---|---|---|---|---|---|
| 5,100,669 | A | * | 3/1992 | Hyon et al. | 424/426 |
| 5,134,122 | A | | 7/1992 | Orsolini | |
| 5,271,945 | A | | 12/1993 | Yoshioka et al. | |
| 5,575,987 | A | | 11/1996 | Kamei et al. | |
| 5,611,971 | A | | 3/1997 | Maedera et al. | |
| 5,716,640 | A | | 2/1998 | Kamei et al. | |
| 5,773,032 | A | | 6/1998 | Engel et al. | |
| 5,851,451 | A | | 12/1998 | Takechi et al. | |
| 5,889,110 | A | * | 3/1999 | Hutchinson | 525/54.1 |
| 6,034,175 | A | | 3/2000 | Hutchinson | |
| 6,036,976 | A | | 3/2000 | Takechi et al. | |
| 6,045,830 | A | | 4/2000 | Igari et al. | |
| 6,113,943 | A | | 9/2000 | Okada et al. | |
| 6,346,274 | B1 | | 2/2002 | Koll et al. | |
| 6,599,519 | B1 | | 7/2003 | Seo et al. | |
| 6,740,634 | B1 | * | 5/2004 | Saikawa et al. | 514/10.1 |
| 2002/0031545 | A1 | | 3/2002 | Okada et al. | |
| 2002/0198315 | A1 | | 12/2002 | Hutchinson | |
| 2003/0134800 | A1 | | 7/2003 | Yamamoto et al. | |
| 2004/0121008 | A1 | | 6/2004 | Shiraishi et al. | |

FOREIGN PATENT DOCUMENTS

| EP | 0 145 240 A2 | 6/1985 |
|---|---|---|
| EP | 0 190 833 A2 | 8/1986 |
| EP | 0 505 966 A1 | 9/1992 |
| EP | 0 586 238 A2 | 3/1994 |
| EP | 0 626 170 A2 | 11/1994 |
| EP | 0 761 213 A2 | 3/1997 |
| EP | 0 779 072 A1 | 6/1997 |
| EP | 0 781 548 A2 | 7/1997 |
| EP | 0 839 525 A1 | 5/1998 |
| EP | 1 197 208 A1 | 4/2002 |
| EP | 1 413 315 A1 | 4/2004 |
| EP | 1 424 080 A1 | 6/2004 |
| JP | 1-216918 A | 8/1989 |
| JP | 1216918 (A) * | 8/1989 |
| JP | 2-124814 A | 5/1990 |
| JP | 2124814 (A) * | 5/1990 |
| JP | 4-208217 A | 7/1992 |
| JP | 4208217 (A) * | 7/1992 |
| JP | 06-065053 | 3/1994 |
| JP | 6-145046 A | 5/1994 |
| JP | 11-116499 | 4/1999 |
| JP | 2000-143533 | 5/2000 |
| JP | 2002-126043 A | 5/2002 |
| JP | 2003-171264 | 6/2003 |
| JP | 2003-252751 | 9/2003 |
| WO | WO 93/24150 | 12/1993 |
| WO | WO 98/32423 | 7/1998 |
| WO | WO 99/12549 | 3/1999 |
| WO | WO 9936099 A1 * | 7/1999 |
| WO | WO 9937288 * | 7/1999 |
| WO | WO 93/24150 * | 4/2000 |
| WO | WO 00/33809 | 6/2000 |
| WO | WO 00/40259 | 7/2000 |
| WO | WO 00/76483 A1 | 12/2000 |
| WO | WO 01/05379 | 1/2001 |
| WO | WO 02/074340 A1 | 9/2002 |
| WO | WO 01/083594 A1 | 1/2003 |
| WO | WO 03/002091 A2 | 1/2003 |
| WO | WO 03/002092 A2 | 1/2003 |
| WO | WO 03/013609 A1 | 2/2003 |
| WO | WO 03/015820 A1 | 2/2003 |

OTHER PUBLICATIONS

Okada, Hiroaki, "Dosage and Design of leuproreline Acetate Microspheres for Long-term Sustained-release Injection", *Pharm Tech Japan*, vol. 14, No. 1, 1998, pp. 75-88.

(Continued)

*Primary Examiner* — Maury Audet
(74) *Attorney, Agent, or Firm* — Foley & Lardner LLP

(57) ABSTRACT

A process for producing a sustained-release composition which comprises mixing an aqueous solution containing a physiologically active substance and an acid or base in a molar amount of 1.5 or more times that of the physiologically active substance with a solution of a biodegradable polymer and then drying the mixture is provided.

20 Claims, 2 Drawing Sheets

OTHER PUBLICATIONS

Woo, Byung H., "In Vitro Characterization and in Vivo Testosterone Suppression of 6-Month Release Poly(D,L-Lactide) Leuprolide Microspheres", *Pharmaceutical Research,* vol. 19, No. 4, Apr. 2002, pp. 546-550.

Office Action mailed Oct. 27, 2009, in corresponding Japanese Application No. 2003-179836, 4 pages, with English translation, 4 pages.

Office Action mailed Feb. 9, 2010, in corresponding Japanese Application No. 2003-179836, 3 pages, with English translation, 3 pages.

Wikipedia: "Fatty acid" retrieved from internet on Jul. 8, 2010, http://en.wikipedia.org/index.php?title=Fatty_acid&printable=yes, 9 pages.

\* cited by examiner

Acetic acid/Drug
Molar Ratio    1.4        1.6        1.8       2.3       2.8

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: 5-oxo-Pro
<220> FEATURE:
<221> NAME/KEY: MOD_RES
<222> LOCATION: (6)..(6)
<223> OTHER INFORMATION: DLeu, DAla, DTrp, DSer(tBu), D2Nal or
      DHis(ImBzl)
<220> FEATURE:
<221> NAME/KEY: MOD_RES
<222> LOCATION: (9)..(9)
<223> OTHER INFORMATION: Pro or Pro-NH-C2H5
<220> FEATURE:
<221> NAME/KEY: MOD_RES
<222> LOCATION: (10)..(10)
<223> OTHER INFORMATION: Gly-NH2 or not present
<220> FEATURE:
<223> OTHER INFORMATION: see specification as filed for detailed
      description of substitutions and preferred embodiments

<400> SEQUENCE: 1

Pro His Trp Ser Tyr Xaa Leu Arg Pro Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may or may not be acetylated
<220> FEATURE:
<221> NAME/KEY: MOD_RES
<222> LOCATION: (1)..(1)
<223> OTHER INFORMATION: N(4H2-furoyl)Gly or absent
<220> FEATURE:
<221> NAME/KEY: MOD_RES
<222> LOCATION: (2)..(2)
<223> OTHER INFORMATION: D2Nal
<220> FEATURE:
<221> NAME/KEY: MOD_RES
<222> LOCATION: (3)..(3)
<223> OTHER INFORMATION: D4ClPhe
<220> FEATURE:
<221> NAME/KEY: MOD_RES
<222> LOCATION: (4)..(4)
<223> OTHER INFORMATION: D3Pal
<220> FEATURE:
<221> NAME/KEY: MOD_RES
<222> LOCATION: (6)..(6)
<223> OTHER INFORMATION: NMeTyr, Tyr, Aph(Atz) or NMeAph(Atz)
<220> FEATURE:
<221> NAME/KEY: MOD_RES
<222> LOCATION: (7)..(7)
<223> OTHER INFORMATION: DLys(Nic), DCit, DLys(AzaglyNic),
      DLys(AzaglyFur), DhArg(Et2), DAph(Atz) or DhCi
<220> FEATURE:
<221> NAME/KEY: MOD_RES
<222> LOCATION: (9)..(9)
<223> OTHER INFORMATION: Lys(Nisp), Arg or hArg(Et2)
<220> FEATURE:
<221> NAME/KEY: MOD_RES
<222> LOCATION: (11)..(11)
<223> OTHER INFORMATION: DAla
<220> FEATURE:
<223> OTHER INFORMATION: C-term amidated
<220> FEATURE:
<223> OTHER INFORMATION: see specification as filed for detailed
      description of substitutions and preferred embodiments

<400> SEQUENCE: 2

Gly Xaa Phe Xaa Ser Xaa Xaa Leu Xaa Pro Ala
1               5                   10

<210> SEQ ID NO 3
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: DLeu
<220> FEATURE:
<221> NAME/KEY: MOD_RES
<222> LOCATION: (9)..(9)
<223> OTHER INFORMATION: Pro-NH-C2H5

<400> SEQUENCE: 3

Pro His Trp Ser Tyr Leu Leu Arg Pro
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: Ser(tBu)
<220> FEATURE:
<221> NAME/KEY: MOD_RES
<222> LOCATION: (9)..(9)
<223> OTHER INFORMATION: Pro-NH-CH2-CH3

<400> SEQUENCE: 4

Pro His Trp Ser Tyr Ser Leu Arg Pro
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<223> OTHER INFORMATION: C-term amidated

<400> SEQUENCE: 5

Pro His Trp Ser Tyr Trp Leu Arg Pro Gly
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: 5-oxo-Pro
<220> FEATURE:
<221> NAME/KEY: MOD_RES
<222> LOCATION: (6)..(6)
<223> OTHER INFORMATION: D2Nal
<220> FEATURE:
<223> OTHER INFORMATION: C-term amidated

<400> SEQUENCE: 6

Pro His Trp Ser Tyr Xaa Leu Arg Pro Gly
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: DHis(ImBzl)
<220> FEATURE:
<221> NAME/KEY: MOD_RES
<222> LOCATION: (9)..(9)
<223> OTHER INFORMATION: Pro-NH-CH2-CH3

<400> SEQUENCE: 7

Pro His Trp Ser Tyr His Leu Arg Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (9)..(9)
<223> OTHER INFORMATION: Pro-NH-CH2-CH2-NH2

<400> SEQUENCE: 8

Pro His Trp Ser Tyr Trp Leu Arg Pro
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: 2MeTrp
<220> FEATURE:
<221> NAME/KEY: MOD_RES
<222> LOCATION: (9)..(9)
```

```
<223> OTHER INFORMATION: Pro-NH-CH2-CH3

<400> SEQUENCE: 9

Pro His Trp Ser Tyr Trp Leu Arg Pro
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<223> OTHER INFORMATION: C-term amidated

<400> SEQUENCE: 10

Pro His Trp Ser Tyr Gly Leu Arg Pro Gly
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: Ser(tBu)
<220> FEATURE:
<221> NAME/KEY: MOD_RES
<222> LOCATION: (9)..(9)
<223> OTHER INFORMATION: Pro-NH-NH-CO-NH2

<400> SEQUENCE: 11

Pro His Trp Ser Tyr Ser Leu Arg Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: D3MeVal
<220> FEATURE:
<221> NAME/KEY: MOD_RES
<222> LOCATION: (9)..(9)
<223> OTHER INFORMATION: Pro-NH-C2H5

<400> SEQUENCE: 12

Pro His Trp Ser Tyr Val Leu Arg Pro
1               5
```

PROCESS FOR PRODUCING SUSTAINED-RELEASE COMPOSITION

TECHNICAL FIELD

The present invention relates to a process for producing a sustained-release composition comprising a physiologically active substance and a biodegradable polymer, a sustained-release composition produced thereby, and the like.

BACKGROUND ART

JP-A 57-118512, JP-A 57-150609 and JP-A 6-145046 disclose a method of producing a sustained-release microcapsule from a W/O type emulsion using a biodegradable polymer.

A sustained-release biodegradable polymer is useful as, for example, a base material for a physiologically active substance-enclosing microcapsule or the like. It is known that polylactic acid, a copolymer of lactic acid and glycolic acid or the like is useful as such a biodegradable polymer (e.g., JP-A 11-269094).

JP-A 7-97334 discloses a sustained-release preparation comprising a physiologically active substance or a salt thereof and a biodegradable polymer having terminal carboxyl, and a process for producing the sustained-release preparation.

An object of the present invention is to provide a process for producing a sustained-release composition which allows stable formation of a W/O type emulsion, a sustained-release composition produced by said process, and the like.

DISCLOSURE OF INVENTION

Under such circumstances, the present inventors intensively studied in order to develop a process for producing a sustained-release composition which allows stable formation of a W/O type emulsion. As a result, they found that a W/O type emulsion can be stabilized by using an aqueous solution containing an excess amount of an acid or base relative to a physiologically active substance. Based on this finding, they further studied and finally completed the present invention.

That is, the present invention provides:
(1) a method for producing a sustained-release composition, which comprises mixing an aqueous solution containing a physiologically active substance and an acid or base in a molar amount of about 1.5 or more times that of the physiologically active substance with a solution of a biodegradable polymer, and then drying the mixture;
(2) the method according to the above (1), wherein the aqueous solution is obtained using a salt of the physiologically active substance with the acid or base;
(3) the method according to the above (1), wherein the proportion of the physiologically active substance in the sustained-release composition is about 0.001 to about 50% by weight;
(4) a method for stabilizing a mixture of an aqueous solution containing a physiologically active substance and a solution of a biodegradable polymer, which comprises adding an acid or base in a molar amount of about 1.5 mol or more times that of the physiologically active substance;
(5) a method for allowing a mixture of an aqueous solution containing a physiologically active substance and a solution of a biodegradable polymer to have a viscosity of about 3,000 cp or less, which comprises adding an acid or base in a molar amount of about 1.5 mol or more times that of the physiologically active substance;
(6) the method according to any one of the above (1), (4) and (5), wherein the physiologically active substance is a physiologically active peptide;
(7) the method according to the above (6), wherein the physiologically active peptide is an LH-RH derivative;
(8) the method according to the above (7), wherein the LH-RH derivative is a compound represented by the general formula:

5-oxo-Pro-His-Trp-Ser-Tyr-Y-Leu-Arg-Pro-Z  (SEQ ID NO: 1)

wherein Y represents DLeu, DAla, DTrp, DSer(tBu), D2Nal or DHis(ImBzl) and Z represents $NH-C_2H_5$ or $Gly-NH_2$;
(9) the method according to any one of the above (1), (4) and (5), wherein the acid or base in a molar amount of about 1.5 to about 5 times that of the physiologically active substance is used;
(10) the method according to any one of the above (1), (4) and (5), wherein the acid or base in a molar amount of about 1.65 to about 3 times that of the physiologically active substance is used;
(11) the method according to any one of the above (1), (4) and (5), wherein the acid is an organic acid;
(12) the method according to the above (11), wherein the organic acid is a fatty acid;
(13) the method according to the above (12), wherein the fatty acid is acetic acid;
(14) the method according to any one of the above (1), (4) and (5), wherein the biodegradable polymer is an α-hydroxycarboxylic acid polymer;
(15) the method according to the above (14), wherein the α-hydroxycarboxylic acid polymer is a lactic acid-glycolic acid polymer;
(16) the method according to the above (15), wherein the molar ratio of lactic acid to glycolic acid in the lactic acid-glycolic acid polymer is 100:0 to 50:50;
(17) the method according to the above (16), wherein the molar ratio of lactic acid to glycolic acid in the lactic acid-glycolic acid polymer is 100:0;
(18) the method according to the above (15), wherein the weight average molecular weight of the lactic acid-glycolic acid polymer is 5,000 to 50,000;
(19) the method according to the above (15), wherein the weight average molecular weight of the lactic acid-glycolic acid polymer is 17,000 to 30,000;
(20) the method according to the above (1), wherein the biodegradable polymer is a lactic acid polymer having a weight average molecular weight of 15,000 to 50,000 and the content of a polymer having a weight average molecular weight of 5,000 or less in said lactic acid polymer is 5% by weight or less;
(21) the method according to the above (1), wherein the biodegradable polymer is a lactic acid-glycolic acid polymer having about 20 to about 1,000 μmol of terminal carboxyl per unit mass (gram) of the polymer;
(22) the method according to the above (1), wherein the molar amount of the terminal carboxyl of the biodegradable polymer is about 0.1 to about 5 times that of the physiologically active substance;
(23) the method according to any one of the above (1), (4) and (5), wherein the solution of a biodegradable polymer is prepared using a low water-soluble organic solvent;
(24) the method according to the above (23), wherein the low water-soluble organic solvent is dichloromethane;
(25) the method according to any one of the above (1), (4) and (5), wherein the mixture is a homogeneous mixture;
(26) the method according to the above (25), wherein the homogenous mixture is an emulsion;

(27) the method according to the above (26), wherein the emulsion is a W/O type emulsion;
(28) the method according to the above (27), wherein the particle size of the W/O type emulsion is very small;
(29) the method according to the above (1), wherein the drying of the mixture is in-water drying;
(30) the method according to the above (29), wherein an aqueous solution of an osmotic pressure regulating agent is used as an outer aqueous phase on the in-water drying;
(31) the method according to the above (30), wherein the osmotic pressure regulating agent is mannitol;
(32) the method according to the above (1), wherein the sustained-release composition is in the form of a microparticle;
(33) the method according to the above (32), wherein the microparticle is a microsphere or a microcapsule;
(34) a method for producing a sustained-release composition, which comprises mixing an aqueous solution containing 1) a physiologically active substance and 2) an acid or base in an amount of about 0.1 to about 20% by weight of said aqueous solution, with a solution of a biodegradable polymer, and then drying the mixture;
(35) the method according to the above (34), wherein the aqueous solution is obtained using a salt of the physiologically active substance with the acid or base;
(36) a sustained-release composition produced by the method according to the above (1);
(37) a use of an aqueous solution containing a physiologically active substance and an acid or base in an amount of about 1.5 or more times the molar amount of the physiologically active substance, for producing a sustained-release preparation containing the physiologically active substance; and the like.

Figure 1:
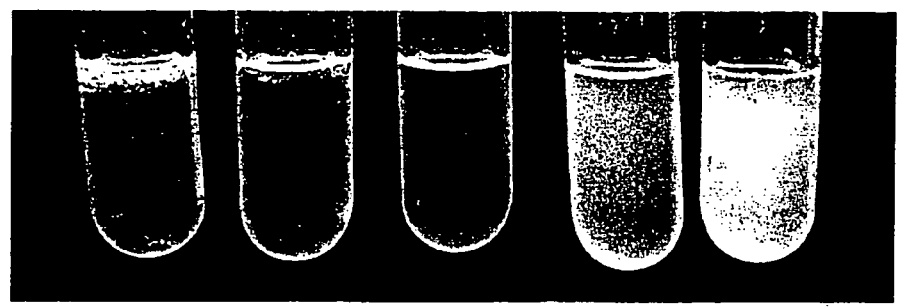
FIG. 1 is a photograph showing the appearance of W/O type emulsions prepared in Experimental Example 2. The numerical values below the photograph represent the molar ratios of acetic acid to a drug.

The cases where the molar ratios of acetic acid to a drug are 1.4, 1.6, 1.8, 2.3 and 2.8 are shown from the left.

A physiologically active substance to be used in the present invention is not particularly limited as long as it is pharmaceutically useful, and may be a non-peptide compound or a peptide compound. Examples of the non-peptide compound include an agonist, an antagonist, and a compound having enzyme inhibiting activity. The peptide compound may be an agonist or an antagonist and may be, for example, preferably a physiologically active peptide, suitably a physiologically active peptide having a molecular weight of about 300 to about 40,000, preferably about 400 to about 30,000, more preferably about 500 to about 20,000.

The proportion of a physiologically active substance in the composition of the present invention varies depending on the kind of a physiologically active substance to be used, the desired pharmacological effect, duration of the effect and the like and not particularly limited. For example, it is about 0.001 to about 50% by weight, preferably about 0.02 to about 40% by weight, more preferably about 0.1 to about 30% by weight, even more preferably about 0.1 to about 24% by weight, most preferably about 5 to about 24% by weight of the total weight of the composition.

Examples of the physiologically active substance include, but not limited to, physiologically active peptides, antitumor agents, antibiotics, antipyretic agents, analgesics, anti-inflammatory agents, antitussive expectorants, sedatives, muscle relaxants, antiepileptic agents, antiulcer agents, antidepressants, anti-allergic agents, cardiotonics, antiarrhythmic agents, vasodilators, hypotensive diuretics, antidiabetics, anticoagulants, hemostatics, antitubercular agents, hormone agents, narcotic antagonists, bone resorption suppressors, and angiogenesis inhibitors.

Examples of the physiologically active peptide include luteinizing hormone-releasing hormone (LH-RH), insulin, somatostatin, growth hormones, growth hormone-releasing hormone (GH-RH), prolactin, erythropoietin, adrenocortical hormone, melanocyte-stimulating hormone, thyroid hormone-releasing hormone (TRH), thyroid-stimulating hormone, luteinizing hormone, follicle-stimulating hormone, vasopressin, oxytocin, calcitonin, gastrin, secretin, pancreozymin, cholecystokinin, angiotensin, human placental lactogen, human chorionic gonadotropin, enkephalin, endorphin, kyotorphin, tuftsin, thymopoietin, thymosin, thymostimulin, thymic humoral factor, blood thymic factor, tumor necrosis factor, colony-stimulating factors, motilin, dynorphin, bombesin, neurotensin, caerulein, bradykinin, atrial natriuretic factor, nerve growth factor, cell growth factor, neurotrophic factor, peptides having endothelin antagonism and derivatives thereof, and fragments thereof and derivatives of such fragments.

The physiologically active peptide may be also an LH-RH antagonist (see U.S. Pat. Nos. 4,086,219, 4,124,577, 4,253, 997, and 4,317,815).

Further examples of the physiologically active peptide include insulin, somatostatin, somatostatin derivatives (see U.S. Pat. Nos. 4,087,390, 4,093,574, 4,100,117, and 4,253, 998), growth hormone, prolactin, adrenocorticotropic hormone (ACTH), melanocyte-stimulating hormone (MSH), thyroid hormone-releasing hormone [represented by the structural formula: (Pyr)Glu-His-ProNH$_2$, hereinafter also referred to as TRH] and salts and derivatives thereof (see JP-A 50-121273 and JP-A 52-116465), thyroid-stimulating hormone (TSH), luteinizing hormone (LH), follicle-stimulating hormone (FSH), vasopressin, vasopressin derivatives [desmopressin, see ENDOCRINE JOURNAL, Vol. 54, No. 5, pp. 676-691 (1978)], oxytocin, calcitonin, parathyroid hormone, glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277,394 and European Patent Publication No. 31567), endorphin, kyotorphin, interferons (e.g., α-, β-, and γ-interferons), interleukins (e.g., I, II, and III), tuftsin, thymopoietin, thymosin, thymostimulin, thymic humoral factor (THF), blood thymic factor (FTS) and a derivative thereof (see U.S. Pat. No. 4,229,438), other thymic factors [Igaku no Ayumi Vol. 125, No. 10, pp. 835-843 (1983)], tumor necrosis factor (TNF), colony-stimulating factor (CSF), motilin, dynorphin, bombesin, neurotensin, cerulein, bradykinin, urokinase, asparaginase, kallikrein, substance P, nerve growth factor, cell growth factor, neurotrophic factor, blood coagulation factors VIII and IX, lysozyme chloride, polymyxin B, colistin, gramicidin, bacitracin, erythropoietin (EPO), and endothelin-antagonistic peptides (see European Patent Publication Nos. 436189, 457195, and 496452 and JP-A 3-94692 and JP-A 3-130299).

Examples of the antitumor agent include bleomycin, methotrexate, actinomycin D, mitomycin C, binblastin sulfate, bincrystin sulfate, daunorubicin, adriamycin, neocartinostatin, cytosine arabinoside, fluorouracil, tetrahydrofuryl-5-fluorouracil, krestin, picibanil, lentinan, levamisole, bestatin, azimexon, glycyrrhizin, polyI:C, polyA:U, and polyICLC.

Examples of the antibiotic include gentamicin, dibekacin, kanendomycin, lividomycin, tobramycin, amikacin, fradiomycin, sisomycin, tetracycline hydrochloride, oxytetracycline hydrochloride, rolitetracycline, doxycycline hydrochloride, ampicillin, piperacillin, ticarcillin, cefalothin, cefaloridine, cefotiam, cefsulodin, cefmenoxime, cefmetazole, cefazolin, cefotaxime, cefoperazon, ceftizoxime, moxalactam, thienamycin, sulfazecin, and aztreonam.

Examples of the antipyretic agent, analgesic and anti-inflammatory agent include salicylic acid, sulpyrine, flufenamic acid, diclofenac, indomethacin, morphine, pethidine hydrochloride, levorphanol tartrate, and oxymorphone.

Examples of the antitussive expectorant include ephedrine hydrochloride, methylephedrine hydrochloride, noscapine hydrochloride, codeine phosphate, dihydrocodeine phosphate, alloclamide hydrochloride, clofedanol hydrochloride, picoperidamine hydrochloride, chloperastine, protokylol hydrochloride, isoproterenol hydrochloride, sulbutamol sulfate, and terbutaline sulfate.

Examples of the sedative include chlorpromazine, prochlorperazine, trifluoperazine, atropine sulfate, and methylscopolamine bromide.

Examples of the muscle relaxant include pridinol methanesulfonate, tubocurarine chloride and pancuronium bromide.

Examples of the antiepileptic agent include phenytoin, ethosuximide, acetazolamide sodium, and chlordiazepoxide.

Examples of the antiulcer agent include metoclopramide and histidine hydrochloride.

Examples of the antidepressant include imipramine, clomipramine, noxiptiline, and phenelzine sulfate.

Examples of the anti-allergic agent include diphenhydramine hydrochloride, chlorpheniramine maleate, tripelennamine hydrochloride, methdilazine hydrochloride, clemizole hydrochloride, diphenylpyraline hydrochloride, and methoxyphenamine hydrochloride.

Examples of the cardiotonic include trans-n-oxocamphor, theophyllol, aminophylline, and etilefrine hydrochloride.

Examples of the antiarrhythmic agent include propranolol, alprenolol, bufetolol, and oxprenolol.

Examples of the vasodilator include oxyfedrine hydrochloride, diltiazem, tolazoline hydrochloride, hexobendine, and bamethan sulfate.

Examples of the hypotensive diuretic include hexamethonium bromide, pentolinium, mecamylamine hydrochloride, ecarazine hydrochloride, and clonidine.

Examples of the antidiabetic include glymidine sodium, glipizide, phenformin hydrochloride, buformin hydrochloride, and metformin.

Examples of the anticoagulant include heparin sodium and sodium citrate.

Examples of the hemostatic include thromboplastin, thrombin, menadione sodium hydrogen sulfite, acetomenaphthone, $\epsilon$-aminocaproic acid, tranexamic acid, carbazochrome sodium sulfonate, and adrenochrome monoaminoguanidine methanesulfonate.

Examples of the antitubercular agent include isoniazid, ethambutol and para-aminosalicylic acid.

Examples of the hormone agent include predonisolone, predonisolone sodium phosphate, dexamethasone sodium sulfate, betamethasone sodium phosphate, hexestrol phosphate, hexestrol acetate, and methimazole.

Examples of the narcotic antagonist include levallorphan tartrate, nalorphine hydrochloride and naloxone hydrochloride.

Examples of the bone resorption suppressor include (sulfur-containing alkyl)aminomethylenebisphosphonic acid.

Examples of the angiogenesis inhibitor include angiogenesis-inhibiting steroids [see Science, Vol. 221, p. 719 (1983)], fumagillin (see European Patent Application Laid-Open No. 325199), and fumagillol derivatives (see European Patent Application Laid-Open Nos. 357061, 359036, 386667 and 415294).

Preferred examples of the physiologically active peptide include LH-RH derivatives effective against hormone-dependent diseases, especially sex hormone-dependent cancer (such as prostatic cancer, uterus cancer, breast cancer, and pituitary tumor) or sex hormone-dependent diseases such as prostatic hypertrophy, endometriosis, hysteromyoma, precocious puberty, dysmenorrhea, amenorrhea, premenstrual syndrome and multilocular ovarian syndrome; LH-RH derivatives effective for contraception (or infertility, if a rebound effect is used after the drug holiday); LH-RH derivatives effective in preventing recurrence of breast cancer after an operation for premenopausal breast cancer; and LH-RH derivatives effective against Alzheimer's disease or immunodeficiency disease; or salts thereof. Additional examples include LH-RH derivatives effective against benign or malignant tumor that is not sex hormone-dependent but sensitive to LH-RH.

Specific examples of the LH-RH derivatives include peptides as disclosed in "Treatment with GnRH analogs: Controversies and perspectives" published by The Parthenon Publishing Group Ltd., 1996, JP-A 3-503165, JP-A 3-101695, JP-A 7-97334 and JP-A 8-259460.

The LH-RH derivative may be an LH-RH agonist or LH-RH antagonist. Examples of an LH-RH antagonist include peptides represented by the general formula [I]:

X-D2Nal-D4ClPhe-D3Pal-Ser-A-B-Leu-C-Pro-DAlaNH$_2$    (SEQ ID NO: 2)

wherein X represents N(4H$_2$-furoyl)Gly or NAc, A represents a residue selected from NMeTyr, Tyr, Aph(Atz) and NMeAph (Atz), B represents a residue selected from DLys(Nic), DCit, DLys(AzaglyNic), DLys(AzaglyFur), DhArg(Et$_2$), DAph (Atz) and DhCi, and C represents Lys(Nisp), Arg or hArg (Et$_2$); abarelix, degarelix, antarelix, iturelix, orntide, cetrorelix, or ganirelix, or a salt thereof.

Examples of a non-peptidic LH-RH antagonist include non-peptidic LH-RH antagonists described in WO 95/28405

(JP-A 8-295693), WO 97/14697 (JP-A 9-169767), WO 97/14682 (JP-A 9-169735) or WO 96/24597 (JP-A 9-169768), thienopyridine compounds (e.g., 3-(N-Benzyl-N-methylaminomethyl)4,7-dihydro-5-isobutyryl-7-(2,6-difluorobenzyl)-2-[4-[(1-hydroxycyclopropyl)carbonylamino] phenyl]-4-oxothieno[2,3-b]pyridine described in WO 00/00493), thienopyrimidine compounds (e.g., 5-(N-benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione described in WO 00/56739), and 5-[(3,5,5,8,8-pentamethyl-5,6,7,8-tetrahydro-2-naphthalenyl) methyl]-N-(2,4,6-trimethoxyphenyl)-2-furamide (American Association for Cancer Research (AACR), 2002. 4.6-10).

Examples of an LH-RH agonist include physiologically active peptides represented by the general formula [II]:

5-oxo-Pro-His-Trp-Ser-Tyr-Y-Leu-Arg-Pro-Z    (SEQ ID NO: 1)

wherein Y represents a residue selected from DLeu, DAla, DTrp, DSer(tBu), D2Nal and DHis(ImBzl) and Z represents NH—$C_2H_5$ or Gly-$NH_2$, and so on. Particularly preferred is a peptide wherein Y is DLeu and Z is NH—$C_2H_5$ (that is, peptide A represented by the formula: 5-oxo-Pro-His-Trp-Ser-Tyr-DLeu-Leu-Arg-Pro-NH—$C_2H_5$ (SEQ ID NO: 3)) or a salt, in particular acetate thereof (leuprorelin acetate).

Preferred specific examples of an LH-RH agonist other than leuprorelin mentioned above include:
(1) Buserelin (SEQ ID NO: 4)

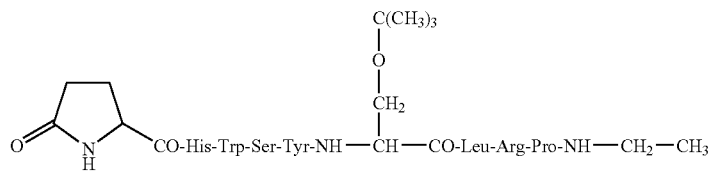

(U.S. Pat. No. 4,024,248, German Patent No. 2438352, JP-A 51-41359);
(2) Triptorelin (SEQ ID NO: 5)

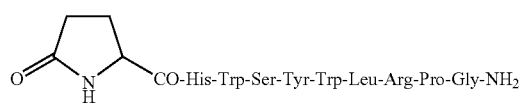

(U.S. Pat. No. 4,010,125, JP-A 52-31073);
(3) Nafarelin (SEQ ID NO: 6)

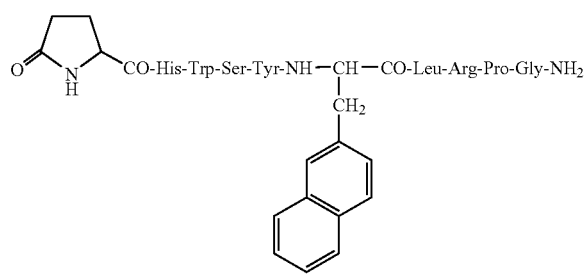

(U.S. Pat. No. 4,234,571, JP-A 55-164663, JP-A 63-264498, JP-A 64-25794);

(4) Histrelin (SEQ ID NO: 7)

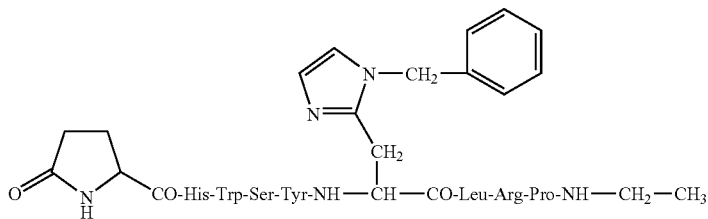

(5) Deslorelin (SEQ ID NO: 8)

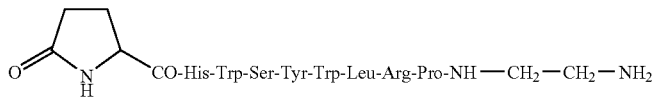

(U.S. Pat. Nos. 4,569,967 and 4,218,439);
(6) Meterelin (SEQ ID NO: 9)

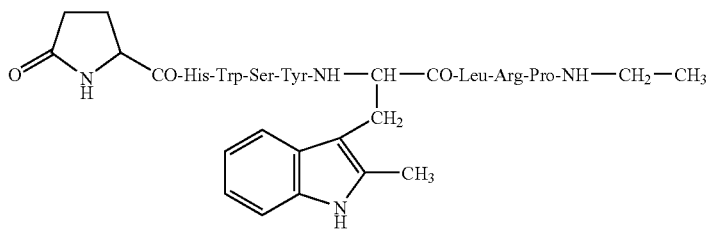

(WO 91/18016);
(7) Gonadrelin (SEQ ID NO: 10)

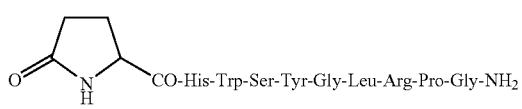

(German Patent No. 2213737);
(8) Goserelin (SEQ ID NO: 11)

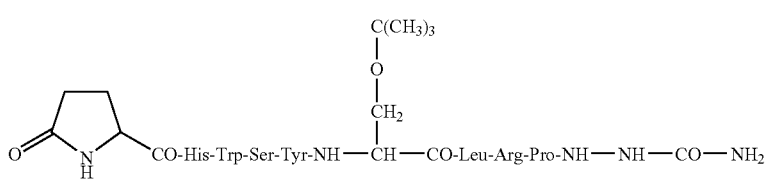

(U.S. Pat. No. 4,100,274, JP-A 52-136172);
(9) Lecirelin (SEQ ID NO: 12)

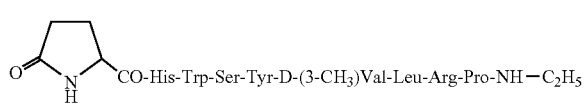

(Belgium Patent No. 897455, JP-A 59-59654); and salts thereof.

The abbreviations used in this specification are defined as follows:

| Abbreviations: | Names |
| --- | --- |
| N(4H$_2$-furoyl)Gly: | N-tetrahydrofuroylglycine residue |
| NAc: | N-acetyl group |
| D2Nal: | D-3-(2-naphthyl)alanine residue |
| D4ClPhe: | D-3-(4-chloro)phenylalanine residue |

-continued

| Abbreviations: | Names |
| --- | --- |
| D3Pal: | D-3-(3-pyridyl)alanine residue |
| NMeTyr: | N-methylthyrosine residue |
| Aph(Atz): | N-[5'-(3'-amino-1'H-1',2',4'-triazolyl)]phenylalanine residue |
| NMeAph(Atz): | N-methyl-[5'-(3'-amino-1'H-1',2',4'-triazolyl)]phenylalanine residue |

-continued

| Abbreviations: | Names |
|---|---|
| DLys(Nic): | D-(e-N-nicotinoyl)lysine residue |
| Dcit: | D-citrulline residue |
| DLys(AzaglyNic): | D-(azaglycylnicotinoyl)lysine residue |
| DLys(AzaglyFur): | D-(azaglycylfuranyl)lysine residue |
| DhArg(Et$_2$): | D-(N,N'-diethyl)homoarginine residue |
| DAph(Atz): | D-N-[5'-(3'-amino-1'H-1',2',4'-triazolyl)]phenylalanine residue |
| DhCi: | D-homocitrulline residue |
| Lys(Nisp): | (e-N-isopropyl)lysine residue |
| hArg(Et$_2$): | (N,N'-diethyl)homoarginine residue |

Abbreviations for other amino acids are according to those defined by the IUPAC-IUB Commission on Biochemical Nomenclature or defined in European Journal of Biochemistry Vol. 138, pp. 9-37, 1984 or according to conventional abbreviations in the field. Although amino acids may have optical isomers, they are represented in L-configuration unless otherwise specified.

The "acid or base" of "an aqueous solution containing a physiologically active substance and an acid or base in a molar amount of about 1.5 or more times that of the physiologically active substance" and "an acid or base in an amount of about 0.1 to about 20% by weight of said aqueous solution", when used in the present invention, may be any acid or base generally used for production and may be an inorganic acid, an organic acid, an inorganic base, an organic base, an acidic or basic amino acid, or the like. The "acid or base" is preferably an acid, more preferably an organic acid.

Preferred examples of an inorganic acid include hydrochloric acid, hydrobromic acid, nitric acid, sulfuric acid and phosphoric acid. Preferred examples of an organic acid include sulfonic acids such as methanesulfonic acid, benzenesulfonic acid and p-toluenesulfonic acid; fatty acids such as formic acid, acetic acid and propionic acid; aliphatic dicarboxylic acids such as oxalic acid, malonic acid and succinic acid; unsaturated fatty acids such as acrylic acid, fumaric acid and maleic acid; carbocyclic carboxylic acids such as phthalic acid, isophthalic acid and terephthalic acid; and substituted carboxylic acids such as trifluoroacetic acid, tartaric acid, citric acid, malic acid, lactic acid and glycolic acid. Among them, fatty acids, lactic acid and glycolic acid are more preferably used, and acetic acid is particularly preferably used. Preferred examples of an acidic amino acid include aspartic acid and glutamic acid. Preferred examples of a basic amino acid include arginine, lysine and ornithine. Preferred examples of an inorganic base include alkali metals such as sodium and potassium; alkaline earth metals such as calcium and magnesium; alkali metal hydrides such as lithium hydride, potassium hydride and sodium hydride; inorganic hydroxides such as lithium hydroxide, potassium hydroxide, sodium hydroxide and calcium hydroxide; carbonates such as sodium carbonate, potassium carbonate and sodium acid carbonate; aluminum, and ammonium. Preferred examples of an organic base include metal alkoxides having 1 to 6 carbon atoms, such as lithium ethoxide, lithium-tert-butoxide, sodium methoxide, sodium ethoxide and potassium-tert-butoxide; metal phenoxides such as potassium phenoxide and sodium phenoxide; acetates such as sodium acetate and potassium acetate; organic lithium salts such as n-butyl lithium, t-butyl lithium and diethylamino lithium; hydrazines such as phenylhydrazine and p-tolylhydrazine; amidines; quaternary ammonium hydroxides; sulfonium bases; and amines such as trimethylamine, triethylamine, pyridine, picoline, 2,6-lutidine, ethanolamine, diethanolamine, triethanolamine, cyclohexylamine, dicyclohexylamine and N,N'-dibenzylethylenediamine.

When the "acid" is an organic acid, its pKa is not particularly limited and it is, for example, preferably in the range of about 0.1 to about 6.0, more preferably in the range of about 1.0 to about 6.0, even more preferably in the range of about 3.5 to about 6.0.

In the present invention, the aqueous solution may contain the "acid or base" independently of a physiologically active substance or in the form of a salt with a physiologically active substance. Alternatively, the aqueous solution may contain both a salt of a physiologically active substance with the "acid or base" and the "acid or base" independent of a physiologically active substance.

As described above, a physiologically active substance may be used as it is or as a pharmacologically acceptable salt thereof in the present invention.

Such a salt includes, when the physiologically active substance has a basic group such as an amino group, salts with inorganic acids (also referred to as inorganic free acids) (e.g., carbonic acid, bicarbonic acid, hydrochloric acid, sulfuric acid, nitric acid, boric acid, etc.) and salts with organic acids (also referred to as organic free acids) (e.g., succinic acid, acetic acid, propionic acid, trifluoroacetic acid, etc.). When the physiologically active substance is an LH-RH derivative, such a salt is preferably acetate. For example, leuprorelin acetate or the like is preferred.

Such a salt includes, when the physiologically active substance has an acidic group such as a carboxyl group, salts with inorganic bases (also referred to as inorganic free bases) (e.g., alkali metals such as sodium and potassium; alkaline earth metals such as calcium and magnesium, etc.) and salts with organic bases (also referred to as organic free bases) (e.g., organic amines such as triethylamine, basic amino acids such as arginine, etc.). The physiologically active peptide may also form a metal complex compound (e.g., a copper complex, a zinc complex, etc.).

These compounds or salts thereof can be produced according to methods described in the above-mentioned literatures or patent gazettes or methods similar to them.

The amount used of the "acid or base" is about 1.5 mol or more, preferably about 1.5 mol to about 5 mol, more preferably about 1.65 mol to about 3 mol per 1 mol of the "physiologically active substance".

In the present invention, the proportion (% by weight) of the "acid or base" in the "aqueous solution" is not particularly limited as long as an effect of the present invention is exerted and is preferably about 0.1 to about 20% by weight, more preferably about 1 to about 15% by weight, even more preferably about 3 to about 10% by weight.

As described above, the "acid or base" may be added independently or in the form of a salt with a physiologically active substance to the aqueous solution. Alternatively, adding the "acid or base" independently and adding a salt of a physiologically active substance with the "acid or base" may be combined.

A biodegradable polymer to be used in the present invention is preferably a biodegradable polymer. Examples of such a biodegradable polymer include aliphatic polyesters [such as homopolymers (e.g., lactic acid polymer) or copolymers (e.g., lactic acid/glycolic acid copolymer and 2-hydroxybutyric acid/glycolic acid copolymer) of two or more of α-hydroxy acids (e.g., glycolic acid, lactic acid, 2-hydroxybutyric acid, 2-hydroxyvaleric acid, 2-hydroxy-3-methylbutyric acid, 2-hydroxycaproic acid, 2-hydroxyisocaproic acid, 2-hydroxycaprylic acid, etc.), cyclic dimers of α-hydroxy acid (e.g., glycolide, lactide, etc.), hydroxydicarboxylic acids (e.g., malic acid) and hydroxytricarboxylic acid (e.g., citric acid), or mixtures of the homopolymers and/or the copolymers (e.g., a mixture of a lactic acid polymer and a 2-hydroxybutyric acid/glycolic acid copolymer, etc.)]; poly-α-cyanoacrylate ester, polyamino acid (e.g., poly-γ-benzyl-L-glutamic acid, poly-L-alanine, poly-γ-methyl-L-glutamic acid, etc.), and maleic anhydride copolymers (e.g., a styrene/maleic acid copolymer, etc.). Preferred are aliphatic polyesters and poly-α-cyanoacrylate esters. Aliphatic polyesters are particularly preferred. Among aliphatic polyesters, preferred are polymers or copolymers having free terminal carboxyl which are synthesized from one or more of α-hydroxycarboxylic acids such as α-hydroxymonocarboxylic acids (e.g., glycolic acid, lactic acid, etc.), α-hydroxydicarboxylic acids (e.g., malic acid) and α-hydroxytricarboxylic acids (e.g., citric acid), or mixtures of these polymers and/or copolymers; poly(α-cyanoacrylic acid esters); polyamino acids (e.g., poly (γ-benzyl-L-glutamic acid), etc.); and maleic anhydride-based copolymers (e.g., a styrene-maleic acid copolymer).

The polymerization type of monomers may be any of random, block and graft types. When the above-mentioned α-hydroxymonocarboxylic acids, α-hydroxydicarboxylic acids, and α-hydroxytricarboxylic acids have an optically active center in their molecular structures, they may be in any of D-, L-, and DL-form. Among them, preferred are lactic acid-glycolic acid polymers [hereinafter, also referred to as poly(lactide-co-glycolide), poly(lactic acid-co-glycolic acid), or lactic acid-glycolic acid copolymer; generically referring to a lactic acid homopolymer, a glycolic acid homopolymer, and a lactic acid-glycolic acid copolymer, unless indicated specifically; or a lactic acid homopolymer is also referred to as a lactic acid polymer, polylactic acid or polylactide, and a glycolic acid homopolymer is also referred to as a glycolic acid polymer, polyglycolic acid, or polyglycolide], and poly(α-cyanoacrylic acid ester). More preferred are lactic acid-glycolic acid polymers, and even more preferred are lactic acid-glycolic acid polymers having free terminal carboxyl.

The biodegradable polymer may be in the form of a salt. Examples of such a salt include salts with inorganic bases (e.g., alkali metals such as sodium and potassium, alkaline earth metals such as calcium and magnesium, etc.), salts with organic bases (e.g., organic amines such as triethylamine, basic amino acids such as arginine, etc.), salts with transition metals (e.g., zinc, iron, copper, etc.) and complex salts.

When a lactic acid-glycolic acid polymer is used as the biodegradable polymer, the composition ratio (mol %) is preferably in the range of 100/0 to about 40/60, more preferably in the range of 100/0 to about 50/50. When the sustained-release composition of the present invention is a long-term sustained-release microcapsule that releases a physiologically active substance over 2 months or more, a lactic acid polymer having a composition ratio of 100/0 is also preferably used.

The optical isomer ratio [D-form/L-form (mol/mol %)] of lactic acid, which is one of the minimum repeat units of the "lactic acid-glycolic acid polymer" is preferably in the range of about 75/25 to about 25/75. In particular, a lactic acid-glycolic acid polymer having a D-form/L-form (mol/mol %) ratio in the range of about 60/40 to about 30/70 is generally used.

The weight average molecular weight of the "lactic acid-glycolic acid polymer" is usually in the range of about 3,000 to about 100,000, preferably in the range of about 5,000 to about 50,000, more preferably in the range of about 8,000 to about 30,000, even more preferably in the range of about 17,000 to about 30,000.

The degree of dispersion (weight average molecular weight/number average molecular weight) is usually in the range of about 1.1 to about 4.0, preferably in the range of about 1.2 to about 3.5. Herein, weight average molecular weights and degrees of dispersion are measured by gel permeation chromatography (GPC). Specifically, the weight average molecular weight means a weight average molecular weight based on polystyrene determined by gel permeation chromatography (GPC) using monodisperse polystyrene as a standard, and the content of each polymer is calculated using the weight average molecular weight thus obtained. Measurements were carried out by using a high-performance GPC apparatus (HLC-8120 GPC, manufactured by Tosoh Corporation) (column: Super H4000×2 and Super H2000 (manufactured by Tosho Corportaion); mobile phase: tetrahydrofuran; flow rate: 0.6 mL/min). Detection is carried out by differential refractometry.

The amount of free terminal carboxyl contained in the "lactic acid-glycolic acid polymer" is preferably about 20 to about 1,000 μmol, more preferably about 40 to about 300 μmol per unit mass (gram) of the polymer.

In the present invention, the molar amount of the free terminal carboxyl of the biodegradable polymer is preferably about 0.1 to about 5 times, more preferably about 0.2 to about 4 times, even more preferably about 0.3 to about 3.5 times that of the "physiologically active substance".

The amount of free terminal carboxyl described above is determined by a labeling method (hereinafter referred to as "the amount of carboxyl as determined by a labeling method"). Specifically, in the case of polylactic acid, W mg of polylactic acid is dissolved in 2 mL of a 5 N hydrochloric acid/acetonitrile (v/v=4/96) mixture, and 2 mL of a 0.01 M solution of o-nitrophenylhydrazine hydrochloride (ONPH) (5 N hydrochloric acid/acetonitrile/ethanol=1.02/35/15) and 2 mL of a 0.15 M solution of 1-ethyl-3-(3-dimethylaminopropyl)-carbodiimide hydrochloride (pyridine/ethanol=4v/96v) are added to react them at 40° C. for 30 minutes. After the solvent is removed, the residue is washed with water (×4) and then dissolved in 2 mL of acetonitrile, and 1 mL of a 0.5 mol/L ethanolic solution of potassium hydroxide is added to react them at 60° C. for 30 minutes. The reaction mixture is diluted with a 1.5 N aqueous solution of sodium hydroxide to Y mL. Absorbance A (/cm) at 544 nm is measured using a 1.5 N aqueous solution of sodium hydroxide as a control. The amount of free carboxyl (C mol/L) thereof is determined by alkali titration with an aqueous solution of DL-lactic acid as a reference substance. When the absorbance at 544 nm of the DL-lactic hydrazide prepared by the ONPH labeling method is defined as B (/cm), the molar amount of free terminal carboxyl per unit mass (gram) of the polymer can be calculated by the following formula:

$$[COOH](mol/g)=(AYC)/(WB).$$

Although "the amount of carboxyl" can also be determined by dissolving the biodegradable polymer in a toluene-acetone-methanol mixed solvent and titrating the solution for a carboxyl group with an alcoholic solution of potassium hydroxide using phenolphthalein as an indicator (hereinafter, a value determined by this method will be referred to as "the amount of carboxyl as determined by an alkali titration method"), it is preferably determined by the labeling method described above because the end point of the titration may be indefinite as a result of competition with hydrolysis of the polyester main chain during titration in the case of the alkali titration method.

The "lactic acid-glycolic acid polymer" can be produced by, for example, catalyst-free dehydration polycondensation from lactic acid and glycolic acid (JP-A 61-28521) or ring-opening polymerization from cyclic diester compounds such as lactide and glycolide by the use of a catalyst (Encyclopedic Handbook of Biomaterials and Bioengineering Part A: Materials, Volume 2, Marcel Dekker, Inc. (1995)). Although a polymer obtained by the above-described known ring-opening polymerization method may not have free terminal carboxyl, it can be modified so as to have some carboxyl groups per unit mass by, for example, hydrolysis reaction described in EP-A-0839525 and then the resulting polymer can be used in the present invention.

The above-described "lactic acid-glycolic acid polymer having free terminal carboxyl" can be produced by a known method (e.g., catalyst-free dehydration polycondensation method; see JP-A 61-28521) or a method pursuant to it.

A polymer used in the present invention is preferably a lactic acid polymer (hereinafter, also referred to as "the lactic acid polymer of the present invention") and examples thereof include a lactic acid homopolymer and copolymers of lactic acid and other monomers (e.g., a copolymer of lactic acid and glycolic acid). In the lactic acid polymer of the present invention, the content of a polymer having a weight average molecular weight of 5,000 or less is usually about 10 wt % or less, preferably about 5 wt % or less, but not limited to them.

The weight average molecular weight of the lactic acid polymer of the present invention is usually in the range of 15,000 to 50,000, preferably in the range of 15,000 to 40,000, more preferably in the range of 17,000 to 30,000.

A high-molecular weight lactic acid polymer to be used as a raw material of the lactic acid polymer of the present invention may be commercially available or prepared by a known polymerization method. The weight average molecular weight of the high-molecular weight lactic acid polymer is usually in the range of 15,000 to 500,000, preferably in the range of 20,000 to 100,000. A known polymerization method includes condensation polymerization of lactic acid together with, if necessary, glycolic acid; ring-opening polymerization of lactide together with, if necessary, glycolide using a catalyst such as Lewis acid (e.g., diethyl zinc, triethylaluminum, tin octylate, etc.) or metal salts; the above described ring-opening polymerization of lactide in the presence of a hydroxycarboxylic acid derivative in which the carboxyl group is protected (e.g., WO 00/35990); ring-opening polymerization of lactide using a catalyst under heating (e.g., J. Med. Chem, 16, 897 (1973)); and copolymerization of lactide and glycolide.

Polymerization is attained by bulk polymerization comprising melting lactide or the like and then subjecting it to polymerization reaction or solution polymerization comprising dissolving lactide or the like in a suitable solvent and then subjecting it to polymerization reaction. It is preferable that a polymer obtained by solution polymerization be used as a raw material of the lactic acid polymer of the present invention from the viewpoint of industrial productivity.

Examples of a solvent to be used for dissolving lactide in solution polymerization include aromatic hydrocarbons such as benzene, toluene and xylene, decalin, and dimethylformamide.

Hydrolysis of the high-molecular weight lactic acid polymer thus obtained is attained by a per se known hydrolysis method. For example, the high-molecular weight lactic acid polymer may be dissolved in a suitable solvent and then reacted in the presence of water and, if necessary, an acid.

Examples of a solvent to be used for dissolving the high-molecular weight lactic acid polymer include halogenated hydrocarbons such as chloroform and dichloromethane; aromatic hydrocarbons such as toluene, o-xylene, m-xylene and p-xylene; cyclic ethers such as tetrahydrofuran; acetone; and N,N-dimethylformamide. When the high-molecular weight lactic acid polymer is produced by polymerization using a solvent that can be also used for hydrolysis of the high-molecular weight lactic acid polymer, the polymerization and hydrolysis can be continuously performed without isolating the high-molecular weight lactic acid polymer after the polymerization.

The amount used of a solvent for dissolving the high-molecular weight lactic acid polymer is usually about 0.1 to about 100 times, preferably about 1 to about 10 times the weight of the high-molecular weight lactic acid polymer, which is the solute.

The amount of water to be added is usually about 0.001 to about 1 time, preferably about 0.01 to about 0.1 time the weight of the high-molecular weight lactic acid polymer.

Examples of an acid to be added if necessary include inorganic acids such as hydrochloric acid, sulfuric acid and nitric acid, and organic acids such as lactic acid, acetic acid and trifluoroacetic acid. Trifluoroacetic acid is preferably used.

The amount of an acid to be added is usually about 0 to about 10 times, preferably about 0.1 to about 1 time the weight of the high-molecular weight lactic acid polymer.

The hydrolysis temperature is usually about 0 to about 150° C., preferably about 20 to about 80° C.

The hydrolysis time varies depending on the weight average molecular weight of the high-molecular weight lactic acid polymer to be used and the reaction temperature, but is usually about 10 minutes to about 100 hours, preferably about 1 to about 20 hours.

Completion of hydrolysis is decided based on the weight average molecular weight of a hydrolysis product. Specifically, samples are appropriately collected during hydrolysis and the weight average molecular weight of a hydrolysis product in the samples is determined by gel permeation chromatography (GPC). When the weight average molecular weight is in the range of about 15,000 to about 50,000, preferably in the range of about 15,000 to about 40,000, more preferably in the range of about 17,000 to about 30,000, hydrolysis is allowed to be terminated.

After the high-molecular weight lactic acid polymer is hydrolyzed as described above, a solution containing a hydrolysis product is obtained. For precipitation of the targeted lactic acid polymer from the solution, a method comprising contacting the hydrolysis product-containing solution with a solvent capable of precipitating the targeted lactic acid polymer contained in the solution, or the like is used.

Preferred aspect of such hydrolysis product-containing solution is, for example, an about 10 to about 50 wt % solution of a lactic acid polymer having a weight average molecular weight of 15,000 to 50,000, preferably 15,000 to 40,000, more preferably 17,000 to 30,000 in a solvent capable of dissolving a high-molecular weight lactic acid polymer, such as halogenated hydrocarbon (e.g., chloroform, dichloromethane, etc.), aromatic hydrocarbon (e.g., toluene, o-xylene, m-xylene, p-xylene, etc.), cyclic ether (e.g., tetrahydrofuran, etc.), acetone, or N,N-dimethylformamide.

Examples of a solvent used for precipitating the targeted lactic acid polymer contained in the hydrolysis product-containing solution include alcohols such as methanol and ethanol, linear ethers such as isopropyl ether, aliphatic hydrocarbons such as hexane, and water.

The amount of a solvent to be used for precipitating the targeted lactic acid polymer is usually about 0.1 to about 100 times, preferably about 1 to about 10 times the weight of the solvent of the hydrolysis product-containing solution.

In a preferred example of a combination of such solvents and their amounts to be used, the solvent of a hydrolysis product-containing solution is dichloromethane in an amount of about 1 to about 5 times the weight of the solute and the solvent for decreasing the solubility of the solute is isopropyl ether in an amount of about 2 to about 10 times the weight of dichloromethane.

When a solvent capable of precipitating the targeted lactic acid polymer solute is contacted with a hydrolysis product-containing solution, the temperature of the solvent is usually about −20 to about 60° C., preferably about 0 to about 40° C. and the temperature of the hydrolysis product-containing solution is usually about 0 to about 40° C., preferably about 10 to about 30° C.

Contacting the solvent with a hydrolysis product-containing solution is attained by adding the hydrolysis product-containing solution into the solvent in one step, adding dropwise the hydrolysis product-containing solution into the solvent, adding the solvent into the hydrolysis product-containing solution in one step, adding dropwise the solvent into the hydrolysis product-containing solution, or the like.

The lactic acid polymer of the present invention thus obtained has terminal carboxyl in a preferred amount for use as a base material for sustained-release preparations, and therefore it is preferably used as a base material for sustained-release preparations. Additional examples of the biocompatible polymer include polystyrene, polymethacrylic acid, a copolymer of acrylic acid and methacrylic acid, polyamino acid, dextran stearate, ethyl cellulose, acetyl cellulose, nitro cellulose, maleic anhydride-based copolymers, ethylenevinylacetate-based copolymers, polyvinyl acetate, and polyacrylamide.

One of these polymers may be used alone, or two or more of these may be used in the form of a copolymer or a simple mixture, or any salt thereof may be used.

Hereinafter, a method of producing a sustained-release composition (e.g., a microcapsule) containing a physiologically active substance or a salt thereof and a lactic acid polymer or a salt thereof according to the present invention will be exemplified.

In the process as described below, the following ingredients (1) to (4) may be added by a per se known method if necessary:

(1) Drug carrier: albumin, gelatin, citric acid, salicylic acid, sodium ethylenediaminetetraacetate, dextrin, sodium hydrogen sulfite, polyol compounds such as polyethylene glycol, agar, alginic acid, polyvinyl alcohol, basic amino acid, or the like;

(2) pH regulator for keeping the stability and solubility of a physiologically active substance or a salt thereof: carbonic acid, acetic acid, oxalic acid, citric acid, phosphoric acid, hydrochloric acid, sodium hydroxide, arginine, lysine, a salt thereof, or the like;

(3) Stabilizer for a physiologically active substance or the salt thereof: albumin, gelatin, citric acid, sodium ethylenediaminetetraacetate, dextrin, sodium hydrogen sulfite, polyol compounds such as polyethylene glycol, or the like;

(4) Preservative: para-hydroxybenzoate esters (e.g., methyl paraben, propyl paraben, etc.), benzyl alcohol, chlorobutanol, thimerosal, or the like.

(I) W/O/W method

In this method, first, a solution of a biodegradable polymer in preferably an organic solvent, more preferably a low water-soluble organic solvent is prepared. The solution for use in producing the sustained-release composition of the present invention (preferably in the form of a microparticle, more preferably in the form of a microsphere or a microcapsule) is preferably a solution in a low water-soluble organic solvent having a boiling point of about 120° C. or less.

Examples of such an organic solvent include halogenated hydrocarbons (e.g., dichloromethane, chloroform, dichloroethane, trichloroethane, carbon tetrachloride, etc.), ethers (e.g., ethyl ether, isopropyl ether, etc.), fatty acid esters (e.g., ethyl acetate, butyl acetate, etc.), aromatic hydrocarbons (e.g., benzene, toluene, xylene, etc.), alcohols (e.g., ethanol, methanol, etc.), and acetonitrile. Among them, preferred are halogenated hydrocarbons and particularly preferred is dichloromethane. These organic solvents may be used in combination at an appropriate ratio. In the case where a mixture of the organic solvents is used, a mixture of halogenated hydrocarbon and alcohol is preferably used, and a mixture of dichloromethane and ethanol is particularly preferably used.

The concentration of the biodegradable polymer in the solution varies depending on the molecular weight of the biodegradable polymer and the kind of the solvent. For example, when dichloromethane is as the solvent, the concentration of the biodegradable polymer is usually about 0.5 to about 70 wt %, preferably about 1 to about 60 wt %, more preferably about 2 to about 50 wt %.

When a mixture of dichloromethane and ethanol is used as the organic solvent, the volume ratio of dichloromethane to ethanol is usually about 0.01 to about 50% (v/v), preferably about 0.05 to about 40% (v/v), more preferably about 0.1 to about 30% (v/v).

Next, as described above, a physiologically active substance is dissolved in an aqueous solution containing an acid or base in a molar amount of about 1.5 times or more that of the physiologically active substance, or in an aqueous solution containing about 0.1 to about 20 wt % of an acid or base. The physiologically active substance may be also dissolved in the form of a salt with a suitable acid or base. The solvent of the aqueous solution may be water or a mixture of water and alcohol (e.g., methanol, ethanol, etc.)

The physiologically active substance or a salt thereof is added so that its concentration in the solution lies usually in the range of about 0.001 mg/mL to about 10 g/mL, preferably about 0.1 mg/mL to about 5 g/mL, more preferably about 10 mg/mL to about 3 g/mL.

Further, a well known solubilizer or stabilizer may be used. For dissolving or dispersing a physiologically active substance and additives, heating, shaking, agitation or the like may be carried out to the extent that the activities thereof are not impaired. The aqueous solution thus obtained is referred to as the inner aqueous phase.

The oil phase and inner aqueous phase thus obtained are emulsified by a well known method such as homogenization or sonication to form a W/O type emulsion.

The biodegradable polymer and the physiologically active substance are mixed so that the amount of the terminal carboxyl (mol) per unit mass (gram) of the biodegradable polymer is usually about 0.01 to about 10 times, preferably about 0.1 to about 5 times the molar amount of the physiologically active substance.

The weight of the oil phase to be mixed is about 1 to about 1,000 times, preferably about 2 to about 100 times, more preferably about 3 to about 30 times the weight of the inner aqueous phase.

The viscosity of the W/O type emulsion thus obtained is usually in the range of about 10 to about 10,000 cp, preferably in the range of about 100 to about 5,000 cp, more preferably in the range of about 200 to about 3,000 cp, even more preferably in the range of about 300 to about 2,000 cp, at about 12 to about 25° C.

When the method of the present invention is employed in industrial production, the viscosity of the W/O type emulsion is preferably in the range of about 3,000 cp or less, more preferably in the range of about 2,000 cp or less, even more preferably in the range of about 300 to about 2,000 cp, at about 12 to about 25° C.

Next, the W/O type emulsion thus obtained is added to an aqueous phase to form a W (inner aqueous phase)/O (oil phase)/W (outer aqueous phase) type emulsion. Thereafter, the solvent in the oil phase is volatilized or diffused into the outer aqueous phase to prepare microcapsules. At this time, the weight of the outer aqueous phase is usually about 1 to about 10,000 times, preferably about 5 to about 5,000 times, more preferably about 10 to about 2,000 times, particularly preferably about 20 to about 500 times the weight of the oil phase.

An emulsifier may be added into the outer aqueous phase. The emulsifier may be usually any emulsifier capable of forming a stable W/O/W type emulsion. Specific examples of such an emulsifier include anionic surfactants (e.g., sodium oleate, sodium stearate, sodium lauryl sulfate, etc.), nonionic surfactants [e.g., polyoxyethylene sorbitan fatty acid esters (e.g., Tween 80 and Tween 60 manufactured by Atlas powder), polyoxyethylene castor oil derivatives (e.g., HCO-60 and HCO-50 manufactured by Nikko Chemicals)], polyvinyl pyrrolidone, polyvinyl alcohol, carboxymethyl cellulose, lecithin, gelatin, and hyaluronic acid. These emulsifiers can be used singly or in combination of two or more of them. The emulsifier is added so that its concentration in the outer aqueous phase lies preferably in the range of about 0.01 to about 10 wt %, more preferably in the range of about 0.05 to about 5 wt %.

An osmotic pressure regulating agent may be added to the outer aqueous phase. Any osmotic pressure regulating agent may be used as long as it can produce an osmotic pressure in an aqueous solution.

Examples of such an osmotic pressure regulating agent include polyhydric alcohols, monohydric alcohols, monosaccharides, disaccharides, oligosaccharides, amino acids, and derivatives thereof.

Examples of the polyhydric alcohol include trihydric alcohols such as glycerin, pentahydric alcohols such as arabitol, xylitol and adonitol, and hexahydric alcohols such as mannitol, sorbitol and dulcitol. Among them, hexahydric alcohol is preferred and mannitol is particularly preferred.

Examples of the monohydric alcohol include methanol, ethanol and isopropyl alcohol. Among them, ethanol is preferred.

Examples of the monosaccharide include pentoses such as arabinose, xylose, ribose and 2-deoxyribose, and hexoses such as glucose, fructose, galactose, mannose, sorbose, rhamnose and fucose. Among them, hexose is preferred.

Examples of the oligosaccharide include trisaccharides such as maltotriose and raffinose, and tetrasaccharides such as stachyose. Among them, trisaccharide is preferred.

Examples of the derivative of monosaccharide, disaccharide or oligosaccharide include glucosamine, galactosamine, glucuronic acid, and galacturonic acid.

The amino acids may be any L-amino acid and examples thereof include glycine, leucine and arginine. Among them, L-arginine is preferred.

These osmotic pressure regulating agents can be used singly or in combination of two or more of them. The osmotic pressure regulating agent is used at such a concentration that the osmotic pressure of the outer aqueous phase is about 1/50 to about 5 times, preferably about 1/25 to about 3 times that of a physiological saline. When mannitol is used as the osmotic pressure regulating agent, its concentration is preferably about 0.5 to about 1.5%.

The organic solvent is removed by a per se known method or a method pursuant to it. Examples of such a method include a method comprising evaporating an organic solvent under normal atmospheric pressure or gradually reduced pressure while stirring with a propeller stirrer, a magnetic stirrer or the like, and a method comprising evaporating an organic solvent under a regulated vacuum with a rotary evaporator or the like.

The microcapsules thus obtained are collected by centrifugation or filtration, washed with distilled water several times to remove the free physiologically active substance, the emulsifier, the osmotic pressure regulating agent and the like adhered to their surfaces, dispersed in distilled water or the like again, and then lyophilized.

An antiflocculant may be added for preventing flocculation of the particles during the process of producing the microcapsules. Examples of such an antiflocculant include mannitol, lactose, glucose, water-soluble polysaccharide such as starch (such as cornstarch), amino acid such as glycine, and protein such as fibrin and collagen. In particular, mannitol is preferred.

The amount of the antiflocculant such as mannitol to be added is usually about 0 to about 24 wt % of the total weight amount of the microcapsules.

After lyophilization, if desired, water and the organic solvent may be removed from the microcapsules by heating under such a condition that the microcapsules are not fused with each other. Preferably, the microcapsules are heated at around the intermediate glass transition temperature of the microcapsules, which is determined with a differential scanning calorimeter at a temperature rising rate of 10° C. to 20° C. per minute, or a slightly higher temperature than the intermediate glass transition temperature of the microcapsules. More preferably, the microcapsules are heated at around their intermediate glass transition temperature to about 30° C. higher temperature than the intermediate glass transition temperature of the microcapsules. Particularly when the biodegradable polymer is a lactic acid-glycolic acid polymer, the microcapsules are preferably heated at around their intermediate glass transition temperature to about 10° C. higher temperature than the intermediate glass transition temperature of the microcapsules, more preferably at around their intermediate glass transition temperature to about 5° C. higher temperature than the intermediate glass transition temperature of the microcapsules.

The heating time varies depending on the amount of the microcapsules or the like. It is generally from about 12 hours to about 168 hours, preferably from about 24 hours to about 120 hours, particularly preferably from about 48 hours to about 96 hours after the microcapsules reach the desired temperature.

A method for heating the microcapsules may be any method capable of heating a population of microcapsules uniformly and is not particularly limited.

Examples of the heat drying method include a method of heat drying in a constant-temperature bath, a fluidized-bed bath, a mobile bath or a kiln and a method of heat drying with a microwave. Preferred is a method of heat drying in a constant-temperature bath.

(II) Phase Separation Method

When microcapsules are produced by this method, a coacervation agent is added slowly to the W/O type emulsion containing a composition composed of a physiologically active substance and a biodegradable polymer as described in the in-water drying method of the above (I) with stirring to precipitate microcapsules, which is then solidified. The amount of the coacervation agent to be added is about 0.01 to about 1,000 times, preferably about 0.05 to about 500 times, particularly preferably about 0.1 to about 200 times the volume of the oil phase.

The coacervation agent includes polymer-based, mineral oil-based, or vegetable oil-based compounds which are miscible with an organic solvent and do not dissolve the biodegradable polymer of the present invention. Specific examples of such a coacervation agent include silicone oil, sesame oil, soybean oil, corn oil, cottonseed oil, coconut oil, linseed oil, mineral oil, n-hexane and n-heptane. They may be used in combination of two or more of them.

The microcapsules thus obtained are collected, washed repeatedly with heptane or the like to remove the coacervation agent and the like other than the composition composed of a physiologically active substance and a biodegradable polymer, and then dried under reduced pressure. Alternatively, the microcapsules may be washed in the same manner as described in the in-water drying method of the above (I), then lyophilized and further heat-dried.

(III) Spray Drying Method

When microcapsules are produced by this method, the W/O type emulsion containing a composition composed of a physiologically active substance and a biodegradable polymer as described in the in-water drying method of the above (I) is sprayed using a nozzle into the drying chamber of a spray drier and the organic solvent contained in the atomized droplets are then volatilized in an extremely short period of time to obtain microcapsules. Examples of such a nozzle include a two-fluid nozzle, a pressure nozzle, and a rotary disc nozzle. Thereafter, if necessary, the microcapsules may be washed in the same manner as described in the in-water drying method of the above (I), then lyophilized and further heat-dried.

As a dosage form other than the above-described microcapsule, a microparticle can be mentioned. Such a microparticle may be prepared in such a manner as described below. First, the organic solvent solution or dispersion containing a composition composed of a physiologically active substance and a biodegradable polymer as described in the in-water drying method of the above (I) is subjected to vacuum drying using, for example, a rotary evaporator or the like to evaporate the organic solvent and water. Next, the residue is ground with a jet mill or the like to obtain microparticles.

In addition, the microparticles may be washed in the same manner as described in the process for producing microcapsules of the above (I), then lyophilized and further heat-dried.

In the present invention, it is preferable that an acid or base in a molar amount of about 1.5 to about 5 times that of a physiologically active substance be used.

When the physiologically active substance is a compound represented by the general formula:

5-oxo-Pro-His-Trp-Ser-Tyr-Y-Leu-Arg-Pro-Z (SEQ ID NO: 1)

wherein each abbreviation represents the same meaning as described above, an acid in a molar amount of about 1.5 to about 5 times that of this physiologically active substance is preferably used. The acid is preferably an organic acid, particularly acetic acid.

The biodegradable polymer is preferably a lactic acid-glycolic acid polymer. The composition ratio (molar ratio) of the lactic acid-glycolic acid polymer is preferably 100:0 to about 50:50, more preferably 100:0. The biodegradable polymer is preferably a lactic acid polymer having a weight average molecular weight of 15,000 to 50,000 wherein the content of a polymer having a weight average molecular weight of 5,000 or less is about 5 wt % or less.

The solution of the biodegradable polymer is preferably prepared using a low water-soluble organic solvent, particularly preferably dichloromethane.

In the present invention, it is preferable that 1) an aqueous solution containing a physiologically active substance and an acid or base and 2) a solution of a biodegradable polymer be mixed homogeneously. More preferably, the mixture thus obtained is an emulsion.

Even more preferably, such an emulsion is a W/O type emulsion wherein the particle size is very small.

Drying of the mixture is preferably carried out by an in-water drying method. In particular, an osmotic pressure regulating agent is preferably added to an outer aqueous phase in the in-water drying method.

The osmotic pressure regulating agent is preferably mannitol.

The sustained-release composition of the present invention may be administered as it is, or as a raw material may be formulated into various dosage forms such as an injection or implant for administration into muscle, subcutis, organ or the like; a transmucosal agent for administration into nasal cavity, rectum, uterus or the like; or an oral agent (such as a capsule (such as a hard capsule and a soft capsule), a solid preparation such as a granule and a powder, and a liquid preparation such as a syrup, an emulsion and a suspension).

For example, the sustained-release composition of the present invention may be mixed with a dispersion medium such as a dispersing agent (e.g., a surfactant such as Tween 80 or HCO-60; polysaccharide such as sodium hyaluronic acid, carboxymethylcellulose or sodium alginate, etc.), a preservative (e.g., methyl paraben, propyl paraben, etc.), and an isotonic agent (e.g., sodium chloride, mannitol, sorbitol, glucose, proline, etc.) to prepare an aqueous suspension, or mixed with a dispersion medium such as a vegetable oil such as sesame oil or corn oil to prepare an oily suspension, so that a practical sustained-release injection can be prepared.

The particle diameter of the sustained-release composition of the present invention for use as a suspension injection should be in such a range that it has a satisfactory dispersibility and a satisfactory ability to pass through a needle. For example, the average particle diameter is in the range of about 0.1 to 300 µm, preferably about 0.5 to 150 µm, more preferably about 1 to 100 µm.

The sustained-release composition of the present invention may be formulated into a sterile preparation by any method including, but not limited to, sterile conditions during all production steps, sterilization with gamma radiation and addition of an antiseptic.

For the above-described sustained-release injection of the sustained-release composition, an excipient (e.g., mannitol, sorbitol, lactose, glucose, etc.) may be added to the components of the above-described suspension, and the resultant suspension may be re-dispersed and then freeze-dried or spray-dried to obtain a solid. At the time of administration, distilled water for injection or any appropriate dispersion medium may be added to the solid to obtain a more stable sustained-release injection.

In the case where an excipient such as mannitol is added to the sustained-release injection of the sustained-release composition, the content of the excipient is from about 0 to 50% by weight, preferably from about 1 to 20% by weight of the whole injection.

In the case where the sustained-release injection of the sustained-release composition is dispersed in distilled water for injection or any appropriate dispersion medium at the time of administration, the content of the sustained-release composition is from about 1 to 80% by weight, preferably from about 10 to 60% by weight of the total amount of the dispersion medium and the sustained-release composition.

The sustained-release composition of the present invention may be formulated into an oral preparation according to a per se known method. For example, the sustained-release composition of the present invention may be mixed with an excipient (e.g., lactose, white sugar, starch, etc.), a disintegrant (e.g., starch, calcium carbonate, etc.), a binder (e.g., starch, gum arabic, carboxymethyl cellulose, polyvinylpyrrolidone, hydroxypropyl cellulose, etc.), a lubricant (e.g., talc, magnesium stearate, polyethylene glycol 6000, etc.)or the like, compression-molded, and then, if necessary, coated by a per se known method for the purpose of masking the taste or giving enteric or sustained-release property to obtain a oral preparation. Examples of such a coating agent include hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (manufactured by Rohm Company, Germany, methacrylic acid-acrylic acid copolymer), and a pigment such as titanium dioxide or colcothar.

The sustained-release composition produced according to the method of the present invention may be formulated into a nasal preparation in the form of a solid, semi-solid or liquid by a per se known method. For example, the solid nasal preparation may be a powdered composition made of the sustained-release composition by itself, or a powdered composition produced by mixing the sustained-release composition with an excipient (e.g., glucose, mannitol, starch, microcrystalline cellulose, etc.), a thickener (e.g., natural gum, a cellulose derivative, an acrylic acid polymer, etc.) or the like, followed by pulverization. The liquid nasal preparation may be produced as an oily or aqueous suspension in a similar manner to the above injection. The semi-solid preparation is preferably produced as an aqueous or oily gel or an ointment. These nasal preparations may contain a pH regulator (e.g., carbonic acid, phosphoric acid, citric acid, hydrochloric acid, sodium hydroxide, etc.), an antiseptic (e.g., para-hydroxybenzoate esters, chlorobutanol, benzalkonium chloride, etc.) or the like.

The sustained-release composition of the present invention may be formulated into a suppository in the form of an oily or aqueous solid or semi-solid or a liquid according to a per se known method. An oily base used for the above suppository may be any oily base that does not dissolve a microcapsule. Examples of such an oily base include glyceride of higher fatty acid [e.g., cacao butter, Witepsol-series products (Dynamite Nobel), etc.], medium fatty acid [e.g., Miglyol-series products (Dynamite Nobel), etc.] and vegetable oil (e.g., sesame oil, soybean oil, cottonseed oil, etc.). Examples of an aqueous base include polyethylene glycol and propylene glycol. Examples of aqueous gel base include natural gums, cellulose derivatives, vinyl polymers and acrylic acid polymers.

The sustained-release composition of the present invention is preferably used as an injection.

The sustained-release composition of the present invention is less toxic and thus can be used as a safe pharmaceutical or the like for a mammal (e.g., human, bovine, swine, dog, cat, mouse, rat, rabbit, etc.).

The dosage of the sustained-release composition of the present invention varies depending on the type and content of a physiologically active substance or a salt thereof as the main drug, the dosage form, the duration of release of a physiologically active substance or a salt thereof, the targeted disease, the targeted animal, or the like, but may be an effective amount of the physiologically active substance or a salt thereof. When the sustained-release composition is a six month preparation, for example, a dose of the physiologically active substance or a salt thereof as the main drug may be selected from the range of about 0.01 mg to about 10 mg/kg, more preferably about 0.05 mg to about 5 mg/kg of body weight for an adult.

A dose of the sustained-release composition may be selected preferably from the range of about 0.05 mg to about 50 mg/kg, more preferably from about 0.1 mg to about 30 mg/kg of body weight for an adult.

The administration frequency may be once every several weeks, once a month, once every several months (e.g., three, four or six months) or the like and appropriately selected depending on the type and content of a physiologically active substance or a salt thereof as the main drug, the dosage form, the duration of release of a physiologically active substance or a salt thereof, the targeted disease, the targeted animal, or the like.

The sustained-release composition of the present invention can be used as an agent for preventing or treating various diseases depending on the type of a physiologically active substance or a salt thereof contained therein. In the case where the physiologically active substance or a salt thereof is an LH-RH derivative, for example, the sustained-release composition of the present invention can be used as an agent for preventing or treating hormone-dependent disease, especially hormone-dependent cancer (e.g., prostatic cancer, uterus cancer, breast cancer, pituitary tumor, etc.) or sex hormone-dependent disease such as prostatic hypertrophy, endometriosis, hysteromyoma, precocious puberty, dysmenorrheal, amenorrhea, premenstrual syndrome, or multilocular ovarian syndrome; an agent for contraception (or for preventing or treating infertility, if a rebound effect is used after the drug holiday); or an agent for preventing or treating disease such as Alzheimer's disease or immunodeficiency. The sustained-release composition of the present invention can also be used as an agent for preventing or treating benign or malignant tumor that is independent of sex hormone but sensitive to LH-RH.

It has been believed that it is difficult to administer a hormone therapy agent including leuprorelin acetate as an agent for preventing postoperative recurrence of breast cancer to a premenopausal patient because some breast cancer cells are sensitive to hormone and are grown by estrogen. However, an agent containing an LH-RH agonist or antagonist (preferably leuprorelin or a salt thereof, more preferably leuprorelin acetate), preferably an agent containing sustained-release microcapsules containing leuprorelin or a salt thereof (preferably leuprorelin acetate), prepared according to the above-described method or a method pursuant to it can be unexpectedly used as an agent for preventing or suppressing postoperative recurrence of premenopausal breast cancer.

An sustained-release composition comprising the above-described agent containing an LH-RH agonist or antagonist (preferably leuprorelin or a salt thereof, more preferably leuprorelin acetate) [preferably the agent containing sustained-release microcapsules containing leuprorelin or a salt thereof (preferably leuprorelin acetate)] can be easily administered as it is in the form of an injection or an implant (preferably an injection) subcutaneously, intramuscularly or intravascualrly (preferably subcutaneously). Such a sustained-release composition can be also formulated into the above-described various dosage forms or may be also used as a raw material in producing such dosage forms.

The dosage of the sustained-release composition containing an LH-RH agonist or antagonist varies depending on targeted disease, the content of the LH-RH agonist or antagonist (preferably leuprorelin or a salt thereof, more preferably leuprorelin acetate), the dosage form, the duration of release of the LH-RH agonist or antagonist (preferably leuprorelin or a salt thereof, more preferably leuprorelin acetate), the targeted animal [e.g., a warm-blooded mammal (e.g., human, mouse, rat, rabbit, sheep, swine, bovine, horse, etc.)] and the like, but may be an effective amount of the LH-RH agonist or antagonist (preferably leuprorelin or a salt thereof, more preferably leuprorelin acetate). For example, a dose of the LH-RH agonist or antagonist (preferably leuprorelin or a salt thereof, more preferably leuprorelin acetate) may be selected from the range of about 0.01 mg to about 100 mg/kg, preferably about 0.02 mg to about 50 mg/kg, more preferably about 0.05 mg to about 20 mg/kg of body weight for a warm-blooded mammal.

In the case where the sustained-release composition containing the LH-RH agonist or antagonist is administered in the form of an injection, usually about 0.01 to about 50 mg, preferably about 0.1 to about 20 mg, more preferably about 0.1 to about 15 mg per month of the LH-RH agonist or antagonist (preferably leuprorelin or a salt thereof, more preferably leuprorelin acetate) may be administered subctaneously or intramuscularly to an adult (60 kg body weight).

The dosing period of the agent containing an LH-RH agonist or antagonist (preferably leuprorelin or a salt thereof, more preferably leuprorelin acetate) [preferably the agent containing sustained-release microcapsules containing leuprorelin or a salt thereof (preferably leuprorelin acetate)] is not particularly limited, but is usually about 1 to 5 years, preferably about 2 years.

For administration to other animals, the above-described dosage per 60 kg body weight may be converted to a dosage per their body weights.

The LH-RH agonist or antagonist [preferably a peptide represented by the formula: 5-oxo-Pro-His-Trp-Ser-Tyr-DLeu-Leu-Arg-Pro-NH—$C_2H_5$ (SEQ ID NO: 3) or a salt thereof (hereinafter, also simply referred to as "leuprorelin or a salt thereof")], more preferably leuprorelin acetate can be administered orally in the form of a tablet optionally coated with sugar, a capsule, elixir or a sustained-release preparation, or parenterally in the form of an injection such as an aseptic solution or suspension in water or a pharmaceutically acceptable liquid other than water, a sustained-release preparation (particularly, a sustained-release microcapsule), an implant (e.g., an implant shaped using a biodegradable polymer as a base material, or an implant prepared by filling an active ingredient into a tube made of a biocompatible metal such as titanium so as to release the active ingredient at a constant rate), an injection prepared by dissolving or dispersing a biodegradable polymer and a drug in an organic solvent acceptable to a living body, or a nasal preparation such as a solution or suspension. It is preferably administered in the form of a sustained-release preparation, particularly preferably in the form of a sustained-release injection. Further, in the case where the sustained-release preparation is a sustained-release microcapsule, the sustained-release microcapsule is preferably a long-term sustained-release microcapsule capable of releasing the LH-RH agonist or antagonist over about 2 months or more.

The above-mentioned preparation can be produced by mixing leuprorelin or a salt thereof, preferably leuprorelin acetate with a known physiologically acceptable carrier, a flavoring agent, an excipient, a vehicle, a preservative, a stabilizer, a binder, and the like in an unit dosage form required for generally accepted pharmaceutical practice.

Additives that may be incorporated into a tablet, a capsule or the like include a binder such as gelatin, corn starch, tragacanth or gum arabic, an excipient such as crystalline cellulose, a swelling agent such as corn starch, gelatin or alginic acid, a lubricant such as magnesium stearate, a sweetening agent such as sucrose, lactose or saccharin, and a flavoring agent such as peppermint, akamono oil or cherry. In the case where the unit dosage form is a capsule, a liquid carrier such as oil and fat may be further incorporated together with the ingredients described above. An aseptic composition for injection may be formulated according to conventional pharmaceutical practice, for example, by dissolving or suspending an active ingredient in a vehicle such as water for injection in naturally occurring vegetable oil such as sesame oil or coconut oil.

An aqueous liquid for injection includes a physiological saline and an isotonic solution containing glucose or other auxiliary agents (e.g., D-sorbitol, D-mannitol, sodium chloride, etc.) and may be used in combination with a suitable solubilizing agent such as alcohol (e.g., ethanol), polyalcohol (e.g., propylene glycol, polyethylene glycol), a nonionic surfactant (e.g., polysorbate 80(TM), HCO-50) or the like. An oily liquid for injection includes sesame oil and soybean oil and may be used in combination with a solubilizing agent such as benzyl benzoate or benzyl alcohol.

The above-described preparation may further contain a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, or the like. The injection thus prepared is usually filled in a suitable sealed container such as an ampule or vial.

EXAMPLES

Hereinafter, the present invention will be described in more detail with reference to Examples.

Example 1

A solution of a DL-lactic acid polymer (weight average molecular weight: 21,900) (206.6 g) in dichloromethane (354.8 g) was adjusted to about 30° C. The solution (381.5 g) was mixed with an aqueous solution of leuprorelin acetate (15.8 g) in aqueous acetic acid (prepared by dissolving 0.6 g of glacial acetic acid in 31.75 g of distilled water) (16.6 g) which had been previously warmed to about 55° C. The mixture thus obtained was emulsified at 10,000 rpm with a minimixer (manufactured by Tokushu Kika Kogyo Co., Ltd.) to obtain a W/O type emulsion. Next, the W/O type emulsion was cooled to about 18° C. and then poured into an aqueous solution (25 L) containing 0.1% (w/w) polyvinyl alcohol (EG-40, manufactured by The Nippon Synthetic Chemical Industry Co., Ltd.) and 1% mannitol which had been adjusted to about 18° C. in advance, which was subjected to secondary emulsification with HOMOMIC LINE FLOW (manufactured by Tokushu Kika Kogyo Co., Ltd.) to obtain a W/O/W type emulsion (turbine rotation rate; about 7,000 rpm, circulating pump rotation rate; about 2,000 rpm). The W/O/W type emulsion was dried in water for about 3 hours, sieved through a standard sieve with 75 μm pore size, and then centrifuged (H-600S, manufactured by Kokusan Enshinki K.K.) (rotation rate; about 2,000 rpm, flow rate; about 600 mL/min) to allow microspheres to settle continuously, which were collected. The collected microspheres were again dispersed in a small amount of distilled water and then sieved through a standard sieve with 90 μm pore size. To the dispersion was added mannitol (18.9 g) and the mixture was freeze-dried with a freeze dryer (TRIOMASTER, manufactured by Kyowa Shinku K.K.) to obtain powder (microsphere powder). The content of leuprorelin acetate in the microsphere thus obtained was 8.2% and the yield was about 75%.

Addition of acetic acid makes it possible to obtain a W/O type emulsion satisfactorily and addition of mannitol into an outer aqueous phase makes it possible to improve the dispersibility of the obtained microspheres.

Experimental Example 1

A solution of a DL-lactic acid polymer (weight average molecular weight: 21,900) (151.3 g) in dichloromethane (259.9 g) was adjusted to about 30° C. The solution (373.7 g) was mixed with an aqueous solution of leuprorelin acetate (15.5 g) in aqueous acetic acid (prepared by dissolving 0.6 g of glacial acetic acid in 31.75 g of distilled water) (16.2 g) which had been previously warmed to about 55° C. The mixture thus obtained was emulsified at 10,000 rpm with a minimixer (manufactured by Tokushu Kika Kogyo Co., Ltd.) to obtain a W/O type emulsion. After 2, 5, and 8 minutes from the beginning of emulsification, a part of the W/O type emulsion was taken and then subjected to viscosity measurement (with a vibration viscometer). The results are shown in Table 1.

TABLE 1

| Emulsification Time | Viscosity | Measurement Temperature |
|---|---|---|
| 2 minutes | 798 cp | 19.7° C. |
| 5 minutes | 1440 cp | 19.7° C. |
| 8 minutes | 2290 cp | 18.9° C. |

As seen in the Table 1, a stable W/O type emulsion was obtained. The W/O type emulsion had a slightly high viscosity after emulsification for 8 minutes. Although the viscosity of the W/O type emulsion after emulsification for 5 minutes was also increased, it was not such a level as to cause a problem in production.

Comparative Example 1

A solution of a DL-lactic acid polymer (weight average molecular weight: 21,900) (151.1 g) in dichloromethane (259.8 g) was adjusted to about 30° C. The solution (374.6 g) was mixed with an aqueous solution of leuprorelin acetate (15.5 g) in distilled water (15.9 g) which had been previously warmed to about 55° C. The mixture thus obtained was emulsified at 10,000 rpm with a minimixer (manufactured by Tokushu Kika Kogyo Co., Ltd.) to obtain a W/O type emulsion. After 2 and 4 minutes from the beginning of emulsification, a part of the W/O type emulsion was taken and then subjected to viscosity measurement (with a vibration viscometer). The results are shown in Table 2.

TABLE 2

| Emulsification Time | Viscosity | Measurement Temperature |
|---|---|---|
| 2 minutes | 1870 cp | 22.1° C. |
| 4 minutes | 4750 cp | 19.9° C. |

The viscosity of the W/O type emulsion was increased after emulsification for 4 minutes. As compared with Experimental Example 1 in which acetic acid was added, the viscosity of the W/O type emulsion was remarkably increased.

Experimental Example 2

Leuprorelin acetate (drug content: 97.4%, acetic acid content: 6.0%) (each 0.2061 g) was dissolved in aqueous acetic acid solutions having various concentrations (each 0.2116 g), and thereto was added a solution of a DL-lactic acid polymer (weight average molecular weight: 21,900) (1.82 g) in dichloromethane (3.15 g). The resulting mixtures were stirred with a vortex mixer for about 30 seconds to obtain W/O type emulsions. The appearances of the W/O type emulsions thus obtained were compared. The results are shown in FIG. 1. In the W/O type emulsion prepared using acetic acid in a molar amount of about 1.8 times that of the drug, it seemed that small emulsion particles were formed. In the W/O type emulsion prepared using acetic acid in a molar amount of about 1.4 times that of the drug, the drug was gelatinized. In the W/O type emulsion prepared using acetic acid in a molar amount of about 1.6 times that of the drug, the drug was slightly gelatinized. Using acetic acid in a molar amount of about 1.8, 2.3 or 2.8 times that of the drug, a homogeneous emulsion was obtained. The W/O type emulsion prepared using acetic acid in a molar amount of about 1.8 times that of the drug had a bluish transparent color. On the other hand, the W/O type emulsion prepared using acetic acid in a molar amount of about 2.3 times or more that of the drug had a whitish emulsion color. The W/O type emulsion prepared using acetic acid in a molar amount of about 1.7 times that of the drug had also a bluish transparent color. From these results, it was found that the smallest emulsion particles were formed in the bluish transparent W/O type emulsion prepared using acetic acid in a molar amount of 1.7 to 1.8 times that of the drug.

Experimental Example 3

Leuprorelin acetate (drug content: 97.4%, acetic acid content: 6.0%) (each 0.2 g) was dissolved in aqueous acetic acid solutions having various concentrations (each 0.2116 g), and thereto was added a solution of a lactic acid-glycolic acid copolymer (weight average molecular weight: 10,500) (1.82 g) in dichloromethane (3.15 g). The resulting mixtures were stirred with a vortex mixer for about 30 seconds to obtain W/O type emulsions. The appearances of the W/O type emulsions thus obtained were compared. As a result, in the W/O type emulsion prepared using acetic acid in a molar amount of about 1.8 times that of the drug, it seemed that homogeneous emulsion particles were formed. In the W/O type emulsions prepared using acetic acid in a molar amount of about 1.3 and 1.4 times that of the drug, the oil phase and the inner aqueous phase were separated.

Experimental Example 4

Leuprorelin acetate (drug content: 97.4%, acetic acid content: 6.0%) (each 0.2 g) was dissolved in aqueous acetic acid solutions having various concentrations (each 0.2116 g), and thereto was added a solution of a DL-lactic acid polymer (weight average molecular weight: 14,500) (1.82 g) in dichloromethane (3.15 g). The resulting mixtures were stirred with a vortex mixer for about 30 seconds to obtain W/O type emulsions. The appearances of the W/O type emulsions thus obtained were compared. As a result, in the W/O type emulsion prepared using acetic acid in a molar amount of about 1.8 times that of the drug, it seemed that homogeneous emulsion particles were formed. In the W/O type emulsions prepared using acetic acid in a molar amount of about 1.3 and 1.4 times that of the drug, the oil phase and the inner aqueous phase were separated.

Experimental Example 5

The microspheres (110 mg) obtained in Example 1 were dispersed in a dispersion medium (0.3 mL) (prepared by dissolving 0.15 mg of carboxymethyl cellulose, 0.3 mg of polysorbate 80 and 15 mg of mannitol in distilled water) and then administered subcutaneously to the backs of 7-week old male SD rats using 22G injection needles. After predetermined times from administration, the rats were slaughtered. Microspheres remaining at the administration site were excised. The content of Peptide A in the microspheres was quantified and the quantitative value was divided by the initial content to determine the remaining rate. The results are shown in Table 3.

TABLE 3

| Remaining rate: Peptide A | |
|---|---|
| 1 day | 96.6% |
| 2 weeks | 89.8% |
| 4 weeks | 84.1% |
| 8 weeks | 73.6% |
| 12 weeks | 56.4% |
| 16 weeks | 44.3% |
| 20 weeks | 18.9% |
| 26 weeks | 3.7% |
| 28 weeks | 2.8% |

As seen in Table 3, the microspheres of Example 1 produced by formulating only Peptide A could contain the physiologically active substance at a high trapping rate, and had excellent dispersibility. Further, the microspheres of Example 1 suppressed initial excessive release of the physiologically active substance and released the physiologically active substance at a constant rate over a very long period of time.

Experimental Example 6

Figure 2:
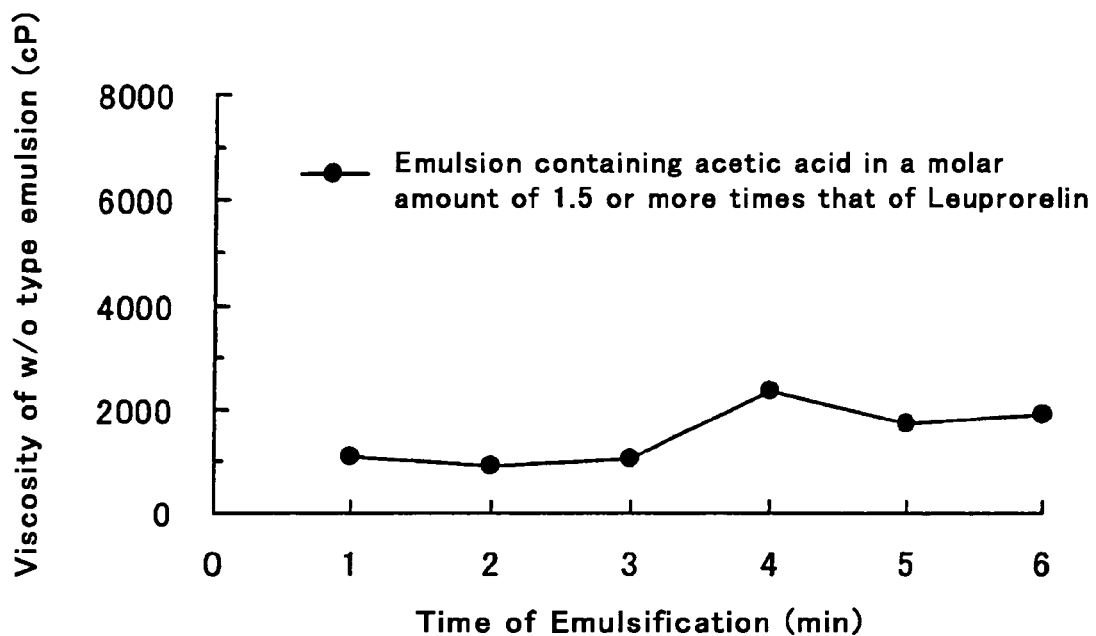
FIG. 2 is a graph showing relationship between the time of emulsification and the viscosity of a W/O type emulsion in a case where acetic acid was used in a molar amount of 1.5 or more times that of peptide A in Experimental Example 6.

An acetic acid salt of Peptide A (0.6 g) was dissolved in a 2 wt % aqueous acetic acid solution (0.65 g) (1.5 times or more the molar amount of Peptide A). To this solution, a solution of polylactic acid (weight average molecular weight; 21,000) (5.4 g) in dichloromethane (9.45 g) was added. The resulting mixture was lightly dispersed by shaking it with a hand and then emulsified with Polytron (manufactured by Kinematica) for a predetermined time to obtain a W/O type emulsion. In the same manner except that the emulsification time was changed to various times, various emulsions were formed. The viscosities of the W/O emulsions thus obtained was measured. The results are shown in FIG. 2.

In the same manner as described above, Peptide A (0.6 g) was dissolved in a 2 wt % aqueous acetic acid solution (0.635 g) (less than 1.5 times the molar amount of Peptide A). To this solution, a solution of polylactic acid (weight average molecular weight; 21,000) (5.4 g) in dichloromethane (9.45 g) was added. The resulting mixture was lightly dispersed by shaking it with a hand and then emulsified with Polytron (manufactured by Kinematica) for a predetermined time to obtain a W/O type emulsion.

The W/O type emulsion prepared using acetic acid in a molar amount less than 1.5 times that of Peptide A had an increased viscosity when the emulsification time was relatively short. On the other hand, the W/O type emulsion prepared using acetic acid in a molar amount of 1.5 times or more that of Peptide A was stable and did not have an increased viscosity even if the emulsification time was short as shown in FIG. 2, so that the W/O type emulsion could be prepared easily.

From these experimental results, it was found that the use of acetic acid in a molar amount of about 1.5 times or more that of a drug made it possible to obtain a stable W/O type emulsion and the use of acetic acid in a molar amount of about 1.65 times or more that of a drug made it possible to obtain an emulsion with relatively smaller particle size. Furthermore, it was confirmed that a lactic acid polymer or a lactic acid-glycolic acid polymer could be used as a polymer for an oil phase, which improved the productivity of final pharmaceuticals.

INDUSTRIAL APPLICABILITY

According to the method for producing a sustained-release composition of the present invention, it is possible to form a W/O type emulsion stably and suppress the leakage of a drug during production, and thus increase productivity of the sustained-release composition. It is also possible to obtain the sustained-release composition wherein a large amount of a drug is incorporated and which is capable of releasing the drug at a constant rate. Furthermore, the sustained-release composition obtained by the method of the present invention is useful as a pharmaceutical because it has a high content of a drug and stable drug-releasing property.

According to the method of the present invention, it is possible to stabilize a mixture of an aqueous solution containing a physiologically active substance and a solution of a biodegradable polymer and obtain such a mixture with a viscosity of 3,000 cp or less under normal conditions.

The present invention is based on the Japanese Patent Application No. 2002-185352 which is herein incorporated by reference as though fully set forth.

The invention claimed is:

1. A method for producing a sustained-release microsphere, which comprises mixing an aqueous solution containing a compound represented by the general formula:

5-oxo-Pro-His-Trp-Ser-Tyr-Y-Leu-Arg-Pro-Z    (SEQ ID NO: 1)

wherein Y represents DLeu, DAla, DTrp, DSer (tBu), D2Nal or DHis (ImBzl) and Z represents NH—$C_2H_5$ or Gly-$NH_2$ and acetic acid in a molar amount of 1.5 to about 5 times that of the compound with a solution of a lactic acid-glycolic acid polymer in a low water-soluble organic solvent to obtain a W/O type emulsion, and then drying the emulsion to obtain microspheres.

2. The method according to claim 1, wherein the aqueous solution is obtained using a salt of the compound with acetic acid.

3. The method according to claim 1, wherein the proportion of the compound in the sustained-release microsphere is about 0.001 to about 50% by weight.

4. A method for stabilizing a W/O type emulsion of an aqueous solution containing a compound represented by the general formula:

5-oxo-Pro-His-Trp-Ser-Tyr-Y-Leu-Arg-Pro-Z    (SEQ ID NO: 1)

wherein Y represents DLeu, DAla, DTrp, DSer (tBu), D2Nal or DHis (ImBzl) and Z represents NH—$C_2H_5$ or Gly-NH, and a solution of a lactic acid-glycolic acid polymer in a low water-soluble organic solvent, which comprises adding to the aqueous solution acetic acid in a molar amount of 1.5 to about 5 times that of the compound.

5. A method for allowing a W/O type emulsion of an aqueous solution containing a compound represented by the general formula:

5-oxo-Pro-His-Trp-Ser-Tyr-Y-Leu-Arg-Pro-Z    (SEQ ID NO: 1)

wherein Y represents DLeu, DAla, DTrp, DSer (tBu), D2Nal or DHis (ImBzl) and Z represents NH—$C_2H_5$ or Gly-$NH_2$ and a solution of a lactic acid-glycolic acid polymer in a low water-soluble organic solvent to have a viscosity of about 3,000 cp or less, which comprises adding to the aqueous solution acetic acid in a molar amount of 1.5 to about 5 times that of the compound.

6. The method according to any one of claims 1, 4 and 5, wherein said acetic acid is used in a molar amount of about 1.65 to about 3 times that of the compound.

7. The method according to claim 1, wherein the molar ratio of lactic acid to glycolic acid in the lactic acid-glycolic acid polymer is 100:0 to 50:50.

8. The method according to claim 1, wherein the molar ratio of lactic acid to glycolic acid in the lactic acid-glycolic acid polymer is 100:0.

9. The method according to claim 1, wherein the weight average molecular weight of the lactic acid-glycolic acid polymer is 5,000 to 50,000.

10. The method according to claim 1, wherein the weight average molecular weight of the lactic acid-glycolic acid polymer is 17,000 to 30,000.

11. The method according to claim 1, wherein the lactic acid-glycolic acid polymer is a lactic acid polymer having a weight average molecular weight of 15,000 to 50,000 and the content of a polymer having a weight average molecular weight of 5,000 or less in said lactic acid polymer is 5% by weight or less.

12. The method according to claim 1, wherein the lactic acid-glycolic acid polymer has about 20 to about 1,000 μmol of terminal carboxyl per unit mass (gram) of the polymer.

13. The method according to claim 1, wherein the molar amount of the terminal carboxyl of the lactic acid-glycolic acid polymer is about 0.1 to about 5 times that of the compound.

14. The method according to any one of claims 1, 4 and 5, wherein the low water-soluble organic solvent is dichloromethane.

15. The method according to claim 1, wherein the drying of the W/O type emulsion is in-water drying.

16. The method according to claim 15, wherein an aqueous solution of an osmotic pressure regulating agent is used as an outer aqueous phase on the in-water drying.

17. The method according to claim 16, wherein the osmotic pressure regulating agent is mannitol.

18. The method according to claim 1, wherein Y represents DLeu and Z represents Gly-$NH_2$.

19. The method according to claim 1, wherein the viscosity of the W/O type emulsion is in the range of about 3,000 cp or less at about 12 to 25° C.

20. The method of claim 1, wherein the W/O type emulsion has a viscosity of 3,000 centipoise (cp) or less under normal conditions.

* * * * *

UNITED STATES PATENT AND TRADEMARK OFFICE
CERTIFICATE OF CORRECTION

PATENT NO.       : 8,088,726 B2                                               Page 1 of 1
APPLICATION NO.  : 10/518914
DATED            : January 3, 2012
INVENTOR(S)      : Kazumichi Yamamoto, Kazuhiro Saito and Tetsuo Hoshino It is certified that error appears in the above-identified patent and that said Letters Patent is hereby corrected as shown below:

Col. 39, claim 4, line 26, "Gly-NH" should be -- Gly-$NH_2$ --.

Signed and Sealed this
Twenty-second Day of May, 2012

David J. Kappos
*Director of the United States Patent and Trademark Office*